US005817751A

United States Patent [19]
Szardenings et al.

[11] Patent Number: 5,817,751
[45] Date of Patent: Oct. 6, 1998

[54] METHOD FOR SYNTHESIS OF DIKETOPIPERAZINE AND DIKETOMORPHOLINE DERIVATIVES

[75] Inventors: Anna Katrin Szardenings, Santa Clara; David Campbell, San Mateo, both of Calif.

[73] Assignee: Affymax Technologies N.V., Greenford, United Kingdom

[21] Appl. No.: 731,362

[22] Filed: Oct. 11, 1996

Related U.S. Application Data

[63] Continuation-in-part of Ser. No. 670,713, Jun. 18, 1996, and a continuation-in-part of Ser. No. 393,318, Feb. 22, 1995, abandoned, which is a continuation-in-part of Ser. No. 265,578, Jun. 23, 1994, abandoned.

[51] Int. Cl.$^6$ ............................... C07K 1/04; C07K 5/12
[52] U.S. Cl. .......................... 530/317; 530/334; 544/170
[58] Field of Search ................................... 530/317, 334; 544/170

[56] References Cited

U.S. PATENT DOCUMENTS

| | | | |
|---|---|---|---|
| 3,752,814 | 8/1973 | Fluckiger et al. | 260/268 |
| 3,752,888 | 8/1973 | Fluckiger et al. | 424/250 |
| 3,923,709 | 12/1975 | Worley | 279/14 |
| 5,147,875 | 9/1992 | Coates et al. | 514/259 |
| 5,164,388 | 11/1992 | De et al. | 514/235.8 |
| 5,288,514 | 2/1994 | Ellman | 427/2 |
| 5,324,483 | 6/1994 | Cody et al. | 422/131 |
| 5,475,013 | 12/1995 | Talley et al. | 514/311 |

FOREIGN PATENT DOCUMENTS

| | | |
|---|---|---|
| WO 92/00091 | 1/1992 | WIPO . |
| WO 95/12608 | 5/1995 | WIPO . |

OTHER PUBLICATIONS

Jun and Beck–Sickinger (1992), "Multiple peptide synthesis methods and their applications," Angewandte Chemie 31:367–383.

Armstrong, R.W. et al., "Multiple–Component Condensation Strategies for Combinatorial Library Synthesis," Acc. Chem. Res. 29:123–131 (1996).

Bertho, J.N. et al., "Amino Acid Fluorides: Their Preparation and Use in Peptide Synthesis," Tetra. Letts. 32(10):1303–1306 (1991).

Brenner, S. et al., "Encoded combinatorial chemistry," Proc. Natl. Acad. Sci. U.S.A. 89:5381–5383 (1992).

Burger, K. et al., "3,3,3–Trifluoro–2–isocyanopropionates, new versatile building blocks for the introduction of trifluoromethyl groups into organic molecules," J. Fluorine Chem. 65:149–152 (1993).

Carpino, L.A. et al., "((9–Fluorenylmethyl)oxy)carbonyl (FMOC) Amino Acid Fluorides. Convenient New Peptide coupling Reagents Applicable to the FMOC/tert–Butyl Strategy for Solution and Solid–Phase Syntheses," J. Am. Chem. Soc. 112:9651–9652 (1990).

Chaturvedi, N.C. et al., "Analogs of Angiotensin II. I. Solid Phase Synthesis," J. Med. Chem. 13:177–181 (1970).

El Marini, A. et al., "Synthesis of Enantiomerically Pure β–and γ–Amino Acids from Aspartic and Glutamic Acid Derivatives," Synthesis pp. 1104–1108 (1992).

(List continued on next page.)

*Primary Examiner*—Cecelia Tsang
*Assistant Examiner*—Bennett Celsa
*Attorney, Agent, or Firm*—Lauren L. Stevens

[57] ABSTRACT

The present invention relates to the areas of organic and medicinal chemistry. More specifically, the present invention is concerned with combinatorial and solid phase methods for the synthesis of diverse diketopiperazine derivatives, and the use of such methods to create libraries of diverse diketopiperazine derivatives. The present invention has application in the areas of chemical synthesis, the screening for new diketopiperazine derivatives having beneficial medical properties and the use of such screening to provide compositions and methods including diketopiperazine derivatives for treating disease.

9 Claims, 5 Drawing Sheets

OTHER PUBLICATIONS

Evans, D.A. et al., "Asymmetric Alkylation Reactions of Chiral Imide Enolates. A Practical Approach to the Enantioselective Synthesis of α–Substituted Carboxylic Acid Derivatives," *J. Amer. Chem. Soc.* 104:1737–1739 (1982).

Giesemann, G. et al., "Synthesis of Chiral α–Isocyano Esters and other Base–sensitive Isocyanides with Oxomethylenebis–(3H⁺–Imidazolium) Bis (methanesulphonate), a Versatile Dehydrating Reagent," *J. Chem. Res. (S)* p. 79 (1982).

Geysen, H.M. et al., "Strategies for epitope analysis using peptide synthesis," *J. Immunological Methods,* 102:259–274 (1987).

Giron–Forest, D.A. et al., "Bromocriptine Methanesulphonate," *Analytical Profiles of Drug Substances,* 8:47–81, Academic Press (1979).

Gokel, G. et al., "Four–Component Condensations and Related Reactions," *Isonitrile Chemistry,* Ugi, I. ed., Academic Press, New York and London, pp. 145–199 (1971).

Hasumi, K. et al., "Lateritin, a new inhibitor of Acyl–CoA–:Cholesterol acyltransferase produced by *Gibberella lateritium* IFO 7188," *J. Antibiotics* 46:1782–1787 (1993).

Horwell, D.C. et al., "The Design of a Dipeptide Library for Screening at Peptide Receptor Sites," *Bioorganic & Medicinal Chemistry Letters* 3(5):799–802 (1993).

Hwang, S.B. et al., "Specific Receptor Sites for 1–O–Alkyl–2–O–acetyl–sn–glycero–3–phosphocholine (Platelet Activating Factor) on Rabbit Platlet and Guinea Pig Smooth Muscle Membranes," *Biochemistry* 22:4756–4763 (1893).

Keating, T.A. et al., "Postcondensation Modifications of Ugi Four–Component Condensation Products: 1–Isocyanocyclohexene as a Convertible Isocyanide. Mechanism of Conversion, Syntghesis of Diverse Structures, and Demonstration of Resin Capture," *J. Am. Chem. Soc.* 118:2574–2583 (1996).

Kim, H.J. et al, "Polymer Attached Cyclic Dipeptides as Catalysts for Enantioselective Cyanohydrin Formation," *Tetrahedron: Asymmetry* 3(11) :1421–1430 (1992).

Kucharczyk, N. et al., "Tetrapeptide Tachykinin Antagonists: Synthesis and Modulation of the Physiocochemical and Pharmacological Properties of a New Seris of Partially Cyclic Analogs," *J. Med. Chem.* 36:1654–1661 (1993).

Leznoff, C.C., The Use of Insoluble Polymer Supports in General Organic Synthesis, *Accounts of Chemical Research* pp. 327–333 (1978).

Palom, Y. et al., "An Acid–Labile Linker for Solid–Phase Oligoribonucleotide Synthesis Using Fmoc Group for 5'–Hydroxyl Protection," *Tetra. Letts.* 34(13) :2195–2198 (1993).

Rajappa, S. et al., "Piperazine–2,5–diones and Related Lactim Ethers," *Adv. Heterocyclic Chem.* 57:187–289 (1993).

Sammes, P.G., "Naturally Occurring 2,5–Dioxopiperazines and Related Compounds," *Fortschritte Der Chemie Organischer Naturstoffe* (*Progress in the Chemistry of Organic Natural Products*) 33:51–118 (1975).

Scott, B.O. et al., "Solid Phase Organic Synthesis (SPOS): A novel route to diketopiperazines and diketomorpholines," *Molecular Diversity* 1(2) :125–134 (1995).

Shen, T.Y. et al., "Characterization of a platelet–activating factor receptor antagonist isolated from haifenteng (*Piper futokadsura*): Specific inhibition of in vitro and in vivo platelet–activating factor induced effects," *Proc. Natl. Acad. Sci. U.S.A.* 82:672–676 (1985).

Shimazaki, N. et al., "Diketopiperazines as a New class of Platelet–Activating Factor Inhibitors," *J. Med. Chem.* 30:1706–1709 (1987).

Shimizaki, N. et al., "Diketopiperazine Derivatives, a New Series of Platelet–Activating Factor Inhibitors," *Chem Pharm. Bull* 35(8) :3527–3530 (1987).

Shiosaki, K. et al., "Toward development of peptidomimetics: Diketopiperazine templates fo the Trp–Met segment of CCK–4," *Peptides: Chemistry Structure and Biology* ESCOM Science Publishers B.V., The Netherlands, pp. 978–980 (1990).

Williams, R.M. et al., "Bicyclomycin: Synthetic, Mechanistic, and Biological Studies," *Chem. Rev.* 88:511–540 (1988).

Winitz, M. et al., "Studies on Diastereoisomeric α–Amino Acids and Corresponding α–Hydroxy Acids. VII. Influence of β–Configuration on Enzymic Susceptibility," *J. Amer. Chem. Soc.* 78:2423–2430 (1956).

Zuckerman, R.N. et al., "Efficient Method for the Preparation of Peptoids [Oligo(N–substituted glycines)] by Submonomer Solid–Phase Synthesis," *J. Am. Chem. Soc.* 114:10646–10647 (1992).

METHOD FOR SYNTHESIS OF DIKETOPIPERAZINE AND DIKETOMORPHOLINE DERIVATIVES

CROSS REFERENCE TO RELATED APPLICATION

This application is a continuation-in-part of U.S. Ser. No. 08/670,713 filed Jun. 18, 1996, and a continuation-in-part of U.S. Ser. No. 08/393,318 filed Feb. 22, 1995 (now abandoned), which is a continuation-in-part of U.S. Ser. No. 08/265,578 filed Jun. 23, 1994 (now abandoned). This application also claims priority under Title 35, United States Code, Section 120 of PCT/US95/07964 filed Jun. 23, 1995 published as WO96/00391, Jan. 4, 1996 (now abandoned). All of the above are herein incorporated by reference.

BACKGROUND OF THE INVENTION

The present invention relates to the areas of organic and medicinal chemistry. More specifically, the present invention is concerned with combinatorial and solid phase methods for the synthesis of diverse diketopiperazine and diketomorpholine derivatives, and the use of such methods in creating libraries of diverse diketopiperazine and diketomorpholine derivatives and homologues. The present invention has application in the areas of chemical synthesis, the screening for new diketopiperazine and diketomorpholine derivatives having beneficial medical properties and the use of such screening to provide compositions and methods including diketopiperazine and diketomorpholine derivatives for treating disease.

Diketopiperazines, also known as 2,5-dioxopiperazines or cyclodipeptides, are some of the most common naturally occurring peptide derivatives (Sammes, P. G. *Fortschr. Chem. Org. Naturst.*, 32:51 (1975)). They are often found among the hydrosylates of proteins and polypeptides and can be isolated from cultures of yeast, lichens and fungi. The generic structure and numbering system of diketopiperazine and diketomorpholine compounds is shown below:

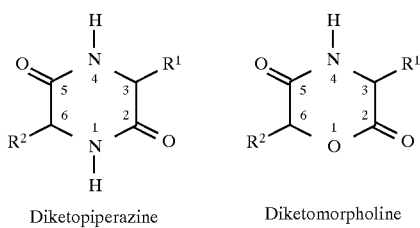

Diketopiperazine    Diketomorpholine

The cyclic structure of these compounds imparts to them unique properties, especially with regards to molecular recognition (Srinivasachari, et al., "Piperazine-2,5-diones and Related Lactim Ethers" in ADVANCES IN HETERCYCLIC CHEMISTRY Vol. 57 pp. 187–260 (Academic Press 1993)). The two amides which comprise the six-membered dipeptide ring of diketopiperazine compounds impart a rigid structure which is capable of forming as many as four hydrogen bonds. These compounds often form a flat ring or a boat configuration in preference to the common chair conformation. This unusual structural motif presents the possibility of designing ring structures having predetermined absolute configurations at two ring atoms in addition to knowledge of the conformations of the ring and side chains. Thus, this class of compounds has come under increasing scrutiny from chemists over the past two decades.

A variety of solution phase techniques have been developed to prepare diketopiperazine ring systems. Generally the alkyl ester of a linear dipeptide, or dipeptide derivative, is cyclized following the removal of a terminal amine protecting group, using acid or base catalysis. Acid catalysis is often preferred as this avoids racemization problems which are associated with base catalysis. These cyclization methods have been used successfully for diketopiperazines having side chain functional groups, such as cyclo-Glu(OBz)-Tyr, cyclo-Gly-Gln, and cyclo-Gln-Arg($NO_2$). Even dipeptides containing residues with acid-labile side chains such as tryptophan have been cyclized successfully under acid catalysis. Base catalysis has also been useful, although it is less often employed as it may lead to racemization of the product.

In certain instances, dipeptides have been cyclized to diketopiperazines under neutral conditions. In these methods, cyclization occurs spontaneously upon deprotection of the terminal amine, or upon heating the unprotected dipeptide in a solvent such as toluene or phenol. Other variations of ring formation without the use of catalysts include the formation of the terminal amine by reduction of the corresponding nitro group followed directly by cyclization. Dipeptide aziridides, presumably formed as intermediates upon reaction of a dipeptide with Leuchs anhydride (1,3-oxazolidine-2,5-dione) and its derivatives, have also been found to cyclize to diketopiperazines. Cyclization following the removal of the amine protecting group from activated ring carboxyl groups has been demonstrated as well. Still another route to diketopiperazines involves the reaction of a-halo dipeptide esters with ammonia. This has been a useful method of synthesizing diketopiperazines having exo-double bonds, such as 3-hydroxyalkylidenepiperzine-2,5-dione. An interesting extension of this last method involves the reaction of a-haloacyl halides with hydrazones to form symmetrical diketopiperazines. This method has been used to generate bicyclic [n.2.2] diketopiperazines. Intramolecular Diels-Alder reactions have been used to form diketopiperazines. For example, reaction of N-sorbylproline with an acylhydrazine to generate the diacylazo derivative followed by oxidation with lead tetraacetate has been shown to provide tricyclic systems containing diketopiperazine rings.

The chemistry of diketopiperazines has also been investigated. Alkylation at one or both of ring nitrogen atoms has been used in the synthesis of gliotoxin and dehydrogliotoxin. Diketopiperazines containing tryptophan have been shown to undergo cyclization under acid catalysis to form pyrroloindoles and hydroxypyrroloindoles. Reaction of diketopiperazines with phosphorous pentasulfide can be used to make the corresponding dithiones. One or both of the ring carbonyl groups may also be reduced to the methylenes. The diketopiperazine ring may be aromatized by reaction with phosphorous oxychloride. Cyclols, thiacyclols and azacyclols have been formed from diketopiperazines. In addition, alkylation at C-3 or C-6 has been used to make bicyclic ring systems containing the diketopiperazine ring system. The anions of the C-3 and C-6 carbons are also known to undergo nucleophilic addition to aldehydes and ketones, as well as nucleophilic substitution reactions and Michael additions. The C-3 and C-6 positions may also be derivatized with thiol or thioester groups which may be joined to form bridges comprising one or more sulfur atoms. Similarly, oxygen substituents have been introduced at C-3 and C-6, including bridgehead oxygen atoms.

Especially interesting classes of diketopiperazine derivatives are the mono- and bis-lactim ethers and thiolactim ethers shown below as I and II respectively ($R_1$ and $R^2$ are any side chain group; $R^3$ and $R^4$ typically are alkyl or aralkyl; X and X' are O or S). Monolactim ethers of formula I with $R^3$ being ethyl or formula II, where $R^3$ and $R^4$ are ethyl are formed by the reaction of a diketopiperazine containing a tertiary amide and a secondary amide with triethyloxonium fluoroborate. Reaction of diketopiperazines having two secondary amino acid constituents with Meerwein's reagent provides bislactim ethers. Thiolactim ethers are made using the corresponding thiolactams. These can undergo additional reactions (1) with secondary amines to produce diaminohydropyrazines, (2) hydrolysis to the constituent amino acid esters, or (3) aromatization. The C-3 and C-6 positions are capable of chemistry similar to that described above. The ability to generate amino acid esters has been used to form novel amino acids.

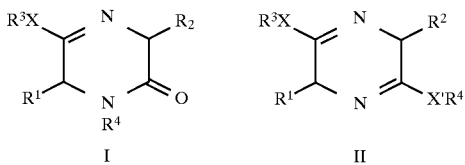

The diketopiperazine ring system is found in a wide variety of compounds having diverse medicinal utility, including dopamine partial agonists, e.g., bromocriptine methansulphonate, (See, e.g., Giron-Forest, et al., "Bromocryptine Methanesulphonate" in ANALYTICAL PROFILES OF DRUG SUBSTANCES, Vol. 8 (Academic Press 1979)). and antibiotics such as bicyclomycin (See, e.g., Williams, et al., *Chem. Rev.* 88:511–540 (1988)). gliotoxin (See Sammes, supra) WS-4545 (See, e.g., U.S. Pat. No. 3,929,790 to Imanaka, et al), and 2-bromo-a-ergocriptine (See, e.g., U.S. Pat. No. 3,752,888 to Fluckiger, et al.), platelet-activating factor antagonists (See, e.g., Hwang, et al., Biochemistry, 88:4756–4763 (1983); Shen, et al., *Proc. Nat. Acad. Sci. USA*, 82:673–676 (1985); Shimazaki, et al., *Chem. Pharm. Bull.* 35(8): 3527–3530 (1987); and Norihiko, et al., *J. Med. Chem.* 30:1706–1709 (1987)), antischizophrenics (See, e.g., Shiosaki, et al., "Towards development of peptidomimetics: Diketopiperazine templates for the Trp-Met segment of CCK-4"), and tachykinin antagonists which have antiinflammatory properties (See, e.g., Kucharczyk, et al., *J. Med. Chem.*, 36:1654–1661 (1993)).

Diketomorpholines are structurally similar to diketopiperazines, and have also been found to possess biological activity. See, Scott et al., Mol. Div. 1(2) 125–134 (1996), Hasumi et al., J. Antibiot. 46:1782–1787 (1993).

Based upon the usefulness of the above-described compounds, it would generally be advantageous to have methods of rapidly and efficiently synthesizing structurally diverse derivatives of these compounds, as well as libraries containing large numbers of these compounds. The present invention meets these and other needs.

SUMMARY OF THE INVENTION

The present invention is generally directed to novel methods of synthesizing diketopiperazine or diketomorpholine derivatives. Typically, the methods of the invention employ a multicomponent reaction for the synthesis of intermediate compounds on solid supports. Cyclization of the intermediate compounds results in formation of the desired diketopiperazine or diketomorpholine derivative, as well as release of the compound from the solid support.

In a first aspect, the present invention provides methods of synthesizing diketopiperazine or diketomorpholine derivatives or homologues. The method generally comprises providing a first amino acid derivative on a solid support. An aldehyde or ketone, an isocyanide, and a compound selected from a free protected amino acid or α-hydroxy acid, are combined with this first amino acid, under conditions whereby a dipeptide (or α-acylamino amide) derivative or α-hydroxy acid (or α-acylhydroxy amide) is formed on the solid support. The support bound precursor is then cyclized to form a diketopiperazine or diketomorpholine derivative, respectively.

In a related aspect, the present invention also provides methods of preparing libraries of diverse diketopiperazine or diketomorpholine derivatives. The method of synthesizing a library of diverse diketopiperazine derivatives comprises providing a first support bound amino acid, partitioning the support bound amino acid into at least two pools. The first pool is combined with a first aldehyde or first ketone, a first isocyanide, and a first free amino acid, to form a first dipeptide (or α-acylamino amide) derivative on the support. The first dipeptide derivative is then cyclized to form a first diketopiperazine derivative. The second pool is then combined with a second aldehyde or ketone, at least a second isocyanide, and at least a second free amino acid, to form at least a second dipeptide derivative on the support, wherein at least one of the second aldehyde or ketone, the second isocyanide, and second free amino acid is different from the first aldehyde or ketone, first isocyanide, first free amino acid and first support bound amino acid, respectively. The second dipeptide derivative is then cyclized to form at least a second diketopiperazine derivative.

The present invention also provides methods of synthesizing dipeptide derivatives or α-hydroxy acid derivatives. For example, provided is a method of synthesizing a compound having the structure:

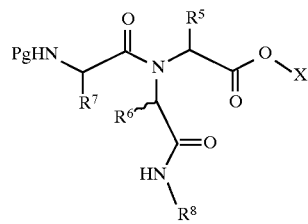

wherein X is a solid support, $R^5$, $R^6$, $R^7$ and $R^8$ are independently selected from hydrogen, alkyl, aryl, heteroaryl, aralkyl, heteroaralkyl, acyl, alkoxyl, aryloxyl, mercapto, alkylthio, arylthio, hydroxyl, cyano, halogen, amino, and amido. Preferred substituents for the amino acid constituents, e.g., $R^5$ and $R^7$, include those found on naturally occurring amino acids, such as benzyl, hydroxymethyl, thiomethyl, methyl, hydrogen, iso-propyl, iso-butyl, imidazolylmethyl, indolylmethyl, 4-aminobutyl, ethoxyl, 2-methylthioethyl, 3-guanidylpropyl, 2-carboxyethyl, 2-amidoethyl, or the like. Other amino acid derivatives include α,α-disubstituted amino acids. The method comprises combining compounds having the following structures:

-continued

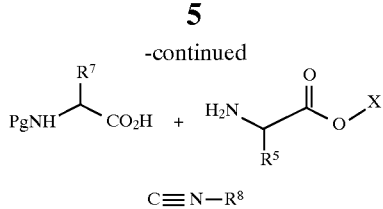

C≡N—R⁸ under conditions conducive to reaction of these compounds.

The present invention also provides methods of preparing homodiketopiperazine derivatives. The methods comprise providing a first amino acid derivative on a solid support. An aldehyde or ketone, an isocyanide, and an anthranilic acid are combined with the support bound amino acid to form a first support-bound intermediate having the structure:

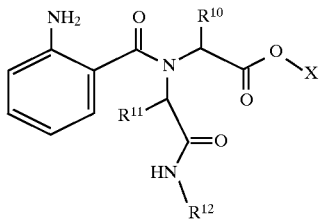

wherein $R^{10}$, $R^{11}$ and $R^{12}$ are independently selected from hydrogen, alkyl, aryl, heteroaryl, aralkyl, heteroaralkyl, acyl, alkoxyl, aryloxyl, mercapto, alkylthio, arylthio, hydroxyl, cyano, halogen, amino, and amido. The support bound intermediate is then cyclized to form a free homodiketopiperazine derivative.

DETAILED DESCRIPTION OF THE INVENTION

I. Terminology

Figure 1:
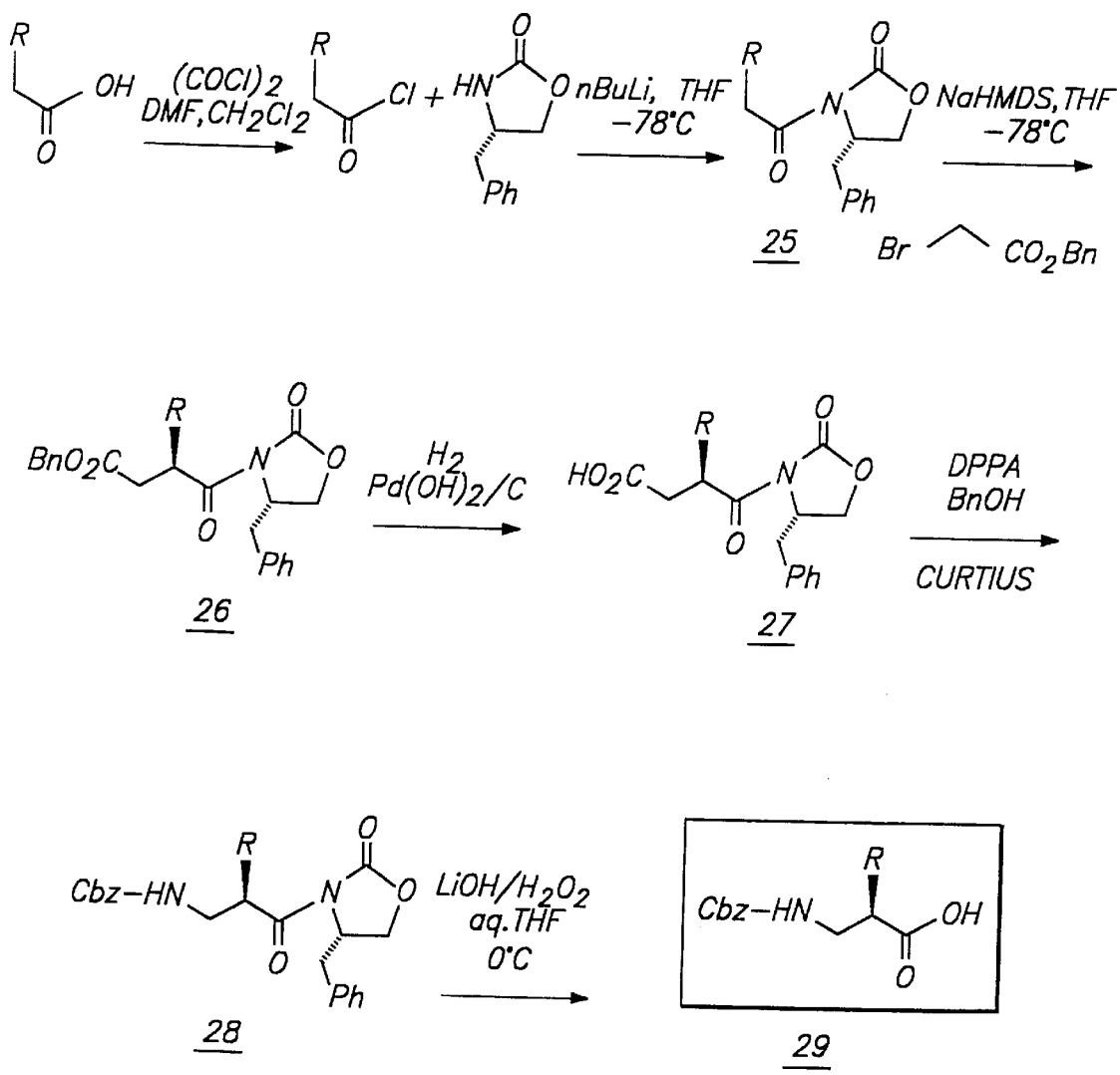
FIG. 1 is a reaction scheme for the preparation of alpha-substituted beta-amino acids.

The following definitions are set forth to illustrate and define the meaning and scope of the various terms used to describe the invention herein. A number of terms and abbreviations are defined to have the general meanings indicated as used herein to describe the invention.

"Activation" or "activating agent" refers to a reagent or energy source which selectively converts a functionality (typically, a carboxyl group) to an activated functionality (typically, an activated ester) which is capable of coupling to a second functionality. For example, carboxyl group can be activated through various means including, but not limited to, the production of the corresponding —OPfp ester through treatment with DCC and pentafluorophenol (see, e.g., Kisfaludy and Schon (1983) Synthesis 325–327) or the trifluoroacetate salt of pentafluorophenoxide and pyridine (see Green and Berman (1990) Tetrahedron Lett. 31:5851–5852). Another preferred form of activated carbonyl is the N-carboxyanhydride group, which can be produced via methods well known in the art. The activated carboxyl group can then be coupled, for example, to an amino group to produce an amide linkage.

"Activated ester" refers to an ester capable of reacting with an amine group to produce an amide linkage. Typically, the carbonyl carbon of an activated ester possesses a higher degree of positive charge character than the carbonyl carbon of an unactivated ester, i.e., a lower alkyl ester.

"Acyl" denotes groups —C(O)R, where R is alkyl or substituted alkyl, aryl, or substituted aryl as defined below.

"Alkyl" or "lower alkyl" refer interchangeably to a cyclic, branched or straight chain, alkyl group of one to eight carbon atoms. This term is further exemplified by such groups as methyl, ethyl, n-propyl, i-propyl, n-butyl, t-butyl, i-butyl (or 2-methylpropyl), cyclopropylmethyl, i-amyl, n-amyl, and hexyl. Preferred groups are methyl, sec-butyl, iso-butyl and iso-propyl. "Substituted lower alkyl" refers to lower alkyl as just described including one or more functional groups such as lower alkyl, aryl, aralkyl, acyl, halogen, hydroxyl, amino, mercapto and the like. These groups may be attached to any carbon atom of the lower alkyl moiety. Preferred groups are 2-guanidinopropyl, 2-carboxymethyl, 2-amidomethyl, thiomethyl, 2-carboxyethyl, 2-amidoethyl, 3-imidazolylmethyl, 4-aminobutyl, 3-hydroxyl-4-aminobutyl, 2-(methylthio) ethyl, hydroxymethyl and 1-hydroxyethyl.

"Alkenyl" generally refers to a lower alkyl substituent having one or more double bonds, such as ethenyl (—CH=CH) and substituted forms thereof. "Alkynyl" refers herein to a lower alkyl substituent having one or more triple bonds, such as ethynyl (—C≡C). "Substituted alkenyl" and "substituted alkynyl" refer to an alkenyl or an alkynyl as just described including one or more functional groups such as lower alkyl, aryl, aralkyl, acyl, halogen, hydroxyl, amino, acylamino, acyloxy, alkoxyl, mercapto and the like.

"Alkoxyl" denotes the group —OR, where R is lower alkyl, substituted lower alkyl, aryl, substituted aryl, aralkyl or substituted aralkyl as defined below.

"Alkylthio" denotes the group —SR, where R is lower alkyl, substituted lower alkyl, aryl, substituted aryl aralkyl or substituted aralkyl as defined below.

"Amido" denotes the group —C(O)NRR', where R and R' may independently be hydrogen, lower alkyl, substituted lower alkyl, aryl, substituted aryl as defined below or acyl.

"Amino" denotes the group NRR', where R and R' may independently be hydrogen, lower alkyl, substituted lower alkyl, aryl, substituted aryl as defined below or acyl.

"Amino Acid Derivative" as used herein, refers generally to both natural and unnatural amino acids, preferably an α- or β-amino acid, which may or may not be modified by the addition of one or more protecting groups, such as 9-fluorenylmethyloxycarbonyl (Fmoc), benzyl or t-butoxycarbonyl (BOC), and/or activating groups or by its coupling to a solid support.

"Aralkyl" refers to the group —R—Ar where Ar is an aryl group and R is straight-chain or branched-chain aliphatic group. Aralkyl groups can optionally be unsubstituted or substituted with, e.g., halogen, lower alkyl, lower alkoxy, lower alkylthio, trifluoromethyl, lower acyloxy, and hydroxy. Preferred aralkyl groups include benzyl, hydroxybenzyl, methylbenzyl, chlorobenzyl, bromobenzyl, iodobenzyl, thiobenzyl, aminobenzyl, napthylmethyl and hydroxynapthylmethyl.

"Aryl" or "Ar" refers to an aromatic carbocyclic group having at least one aromatic ring (e.g., phenyl or biphenyl) or multiple condensed rings in which at least one ring is aromatic, (e.g., 1,2,3,4-tetrahydronaphthyl, naphthyl, anthryl, or phenanthryl). Preferred substituents are phenyl and napthyl. "Substituted aryl" refers to aryl optionally substituted with one or more functional groups, e.g., halogen, lower alkyl, lower alkoxyl, lower alkylthio, trifluoromethyl, lower acyloxyl, hydroxyl and the like. Preferred groups include methylphenyl, chlorophenyl, iodophenyl, bromophenyl, 4-hydroxyphenyl, thiophenyl, 4-chlorothiophenyl, 2-methylthiophenyl and 4-methylsulfonylphenyl.

"Aryloxyl" denotes groups —OAr, where Ar is an aryl or substituted aryl group as defined below.

"Dipeptide Derivative" refers to a dipeptide which has been modified by the addition of one or more protecting groups, such as 9-fluorenylmethyloxycarbonyl (Fmoc), benzyl or t-butoxycarbonyl (BOC), and/or activating groups or by its coupling to a solid support.

"Diketopiperazine derivative" or "Diketomorpholine derivative" refers generally to compounds having the general chemical structure shown above for diketopiperazines and diketomorpholines.

"Exogenous base" refers to nonnucleophilic bases such as alkali metal acetates, alkali metal carbonates, alkaline metal carbonates, alkali metal bicarbonates, tri(lower alkyl) amines, and the like, for example, sodium acetate, potassium bicarbonate, calcium carbonate, diisopropylethylamine, triethylamine, and the like.

"Halogen" refers to bromine, chlorine, and/or iodine atoms.

"Heteroaryl" or "HetAr" refers to an aromatic carbocyclic group having a single ring (e.g., pyridyl or furyl) or multiple condensed rings (e.g., naphthyridinyl, quinoxalyl, quinolinyl, indolizinyl or benzo[b]thienyl) and having at least one hetero atom, such as N, O or S, within the ring. "Substituted heteroaryl refers to heteroaryl substituted with, e.g., halogen, lower alkyl, lower alkoxy, lower alkylthio, trifluoromethyl, lower acyloxy, and hydroxy. Preferred heteroaryl groups include indolyl, methylindolyl, imidazolyl, N-methylimidazolyl and methylimidazolyl.

"Heteroarylalkyl" refers to the group —R—HetAr where HetAr is an heteroaryl group and R is straight-chain or branched-chain aliphatic group. Heteroarylalkyl groups can optionally be unsubstituted or substituted with, e.g., halogen, lower alkyl, lower alkoxyl, lower alkylthio, trifluoromethyl, lower acyloxy, and hydroxy. Preferred heteroaralkyl groups include 3-indolylmethyl and 2-imidazolylmethyl.

"Hydroxyl" refers to the group —OH.

"Cleavable linking arms" refer to linking arms wherein at least one of the covalent bonds of the linking arm which attaches the compound comprising the diketopiperazine group to the solid support can be readily broken by specific chemical reactions thereby providing for compounds comprising diketopiperazine groups free of the solid support ("soluble compounds"). The chemical reactions employed to break the covalent bond of the linking arm are selected so as to be specific for bond breakage thereby preventing unintended reactions occurring elsewhere on the compound. The cleavable linking arm is selected relative to the synthesis of the compounds to be formed on the solid support so as to prevent premature cleavage of this compound from the solid support as well as not to interfere with any of the procedures employed during compound synthesis on the support.

Suitable cleavable linking arms are well known in the art and include those described in U.S. application Ser. No. 08/393,318.

Reversible covalent cleavable linkages can be used to attach the molecules to the support. Examples of suitable reversible chemical linkages include (1) a sulfoester linkage provided by, e.g., a thiolated tagged-molecule and a N-hydroxy-succinimidyl support, which linkage can be controlled by adjustment of the ammonium hydroxide concentration; (2) an benzylhydryl or benzylamide linkage provided by, e.g., a Knorr linker, which linkage can be controlled by adjustment of acid concentration; (3) a disulfide linkage provided by, e.g., a thiolated tagged-molecule and a 2-pyridyl disulfide support (e.g., thiolsepharose from Sigma), which linkage can be controlled by adjustment of the DTT (dithiothreitol) concentration; and (4) linkers which can be cleaved with a transition metal (i.e. HYCRAM).

The linker may be attached between the tag and/or the molecule and the support via a non-reversible covalent cleavable linkage. For example, linkers which can be cleaved photolytically can be used. Preferred photocleavable linkers of the invention include 6-nitroveratryoxycarbonyl (NVOC) and other NVOC related linker compounds (see PCT patent publication Nos. WO 90/15070 and WO 92/10092; see also U.S. patent application Ser. No. 07/971, 181, filed 2 Nov. 1992, incorporated herein by reference); the ortho-nitrobenzyl-based linker described by Rich (see Rich and Gurwara (1975) *J. Am. Chem. Soc.* 97:1575–1579; and Barany and Albericio (1985) *J. Am. Chem. Soc.* 107: 4936–4942) and the phenacyl based linker discussed by Wang. (see Wang (1976) *J. Org. Chem.* 41:3258; and Bellof and Mutter (1985) *Chimia* 39:10). Other particularly preferred photocleavable linkers are described in copending patent application Ser. No. 08/493,877, filed Jun. 23, 1995, and PCT Publication No. PCT/US95/07985, filed Jun. 23, 1995.

"Non-cleavable linking arms" refer to linking arms wherein one or more of the covalent bonds linking the compound comprising a diketopiperazine to the solid support can only be cleaved under conditions which chemically alters unintended parts of the structure of the compound attached thereto.

"Stereoisomer" refers to a chemical compound having the same molecular weight, chemical composition, and constitution as another, but with the atoms grouped differently. That is, certain identical chemical moieties are at different orientations in space and, therefore, when pure, has the ability to rotate the plane of polarized light. However, some pure stereoisomers may have an optical rotation that is so slight that it is undetectable with present instrumentation. The compounds of the present invention may have one or more asymmetrical carbon atoms and therefore include various stereoisomers. All stereoisomers are included within the scope of the invention.

"Substantially Homogeneous" refers to collections of molecules wherein at least about 80%, preferably about 90% and more preferably about 95%, of the molecules are a single compound or stereoisomer therof.

"Substrate" or "support" refers to a material or group of materials having rigid or semi-rigid structures. These materials may take the form of beads, gels, resins, pins, microspheres, rings, of flat surfaces. The substrate or support surface may further be divisible into two or more regions upon which chemically diverse structures may be bound. Other forms will be known to those of skill in the art.

"Thiol" or "mercapto" refers to the group —SH.

The following abbreviations will be used herein. It will be recognized that these abbreviations are of common usage in the chemical arts.

| | |
|---|---|
| BOC: | t-Butoxycarbonyl. |
| BOP: | Benzotriazol-1-yl-oxytris(dimethylamino)phosphonium hexafluorophosphate. |
| PyBOP: | Benzotriazol-1-yl-oxytris(pyrrolidino)phosphonium hexafluorophosphate. |
| DCM: | Dichloromethane |
| DCC: | Dicyclohexylcarbodiimide. |
| Fmoc: | Fluorenylmethyloxycarbonyl. |
| TFA: | Trifluoroacetic acid. |
| DMF: | Dimethylformamide. |
| DIEA: | Diisopropylethylamine. |
| TEA: | Triethylamine. |
| DBU: | 1,8-Diazabicyclo[5.4.0]undec-7-ene. |
| DMAP: | N,N-Dimethylaminopyridine. |
| DIC: | Diisopropylcarbodiimide. |
| HOBT: | 1-Hydroxybenzotriazole. |
| HATU: | [O-(7-Azabenzotriazol-1-yl)-1,1,3,3-tetramethyl-uronium]hexafluorophosphate. |
| HBTU: | 2-(1H-benzotriazol-1-yl)-1,1,3,3-tetramethyl-uroniumhexafluorophosphate. |
| Trt: | Triphenylmethyl or trityl. |
| DMSO: | Dimethylsulfoxide. |
| NMP: | N-Methylpyrrolidine. |
| OTf: | Trifluoromethanesulfonate, e.g.: |

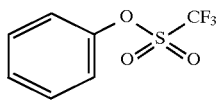

II. Overview

The present invention generally provides novel methods of synthesizing diverse diketopiperazine and diketomorpholine derivatives, as well as homologues and derivatives thereof. Methods of synthesizing diketopiperazines in either soluble or support-bound form have been described in copending U.S. patent application Ser. No. 08/393,318, filed Feb. 22, 1995, which is hereby incorporated herein by reference, in its entirety for all purposes. For each of the methods of diketopiperazine synthesis described herein, a first amino acid derivative is attached to a solid support to form a bound first amino acid derivative. The bound first amino acid derivative is then reacted, concurrently (e.g., in a one pot reaction) with a second amino acid derivative, an aldehyde or ketone and an isocyanate, under conditions effective to form a peptide bond, so that a bound dipeptide (or α-acylamino amide) derivative is formed. This bound dipeptide derivative is then reacted under conditions effective to cyclize the bound derivative to form a free diketopiperazine derivative. Soluble N-alkylated diketopiperazines are then produced via cyclization of the dipeptide derivative and concomitant cleavage from the resin. Components common to each of these methods are described below, followed by more detailed descriptions of the specific embodiments. For synthesis of diketomorpholine derivatives, the support bound amino acid is substituted with a support bound α-hydroxy acid (or α-acylhydroxy amide). These methods also generally may be modified to produce diverse libraries of these compounds.

A. Amino Acids and Derivatives Thereof

The methods of the present invention produce diketopiperazines, homodiketopiperazines, diketomorpholines and derivatives thereof, typically from the coupling of two amino acids, or an amino acid and an α-hydroxy acid. The amino acids and derivatives thereof used in the present invention include the twenty naturally occurring α-amino acids, in either their D- or L-enantiomeric forms. Unnatural amino acids such as α,α-disubstituted amino acids, N-alkyl amino acids, lactic acid, and other unconventional amino acids are also suitable components for the diketopiperazines of the present invention. Examples of unnatural amino acids include: 4-hydroxyproline, O-phosphoserine, 3-methylhistidine, 5-hydroxylysine, and other similar amino acids and imino acids (e.g., 4-hydroxyproline). Thus, the present invention includes methods for synthesizing diketopiperazines such as cyclo-L-Ala-L-Lys in addition to its unnatural derivatives, such as, cyclo-L-Ala-L-(5-hydroxyLys). Thus, the present invention specifically includes the use of all α-amino acid derivatives in addition to the derivatives of the twenty naturally occurring amino acids just described. Techniques for making α-amino acids are well known in the chemical arts and are described in such common references as, e.g., those by Williams, R. Synthesis of Optically Active α-Amino Acids (Pergammon, 1989)

Amino acid side chains of the amino acid may include hydrogen, alkyl, aryl, heteroaryl, aralkyl, heteroaralkyl, acyl, alkoxyl, aryloxyl, mercapto, alkylthio, arylthio, hydroxyl, cyano, halogen, amino, and amido. Preferred substituents are any of those found on naturally occurring amino acids, such as benzyl, hydroxymethyl, thiomethyl, methyl, hydrogen, iso-propyl, iso-butyl, imidazolylmethyl, indolylmethyl, 4-aminobutyl, ethoxyl, 2-methylthioethyl, 3-guanidylpropyl, 2-carboxyethyl, 2-amidoethyl, or the like. Other amino acid derivatives include α,α-disubstituted amino acids.

According to some embodiments, the side chain of at least one of the amino acid derivatives will comprise a chelation group. A chelation group is a chemical functionality or a combination of chemical functionalities which are capable of forming coordination complexes with metal ions, for example, $Cu^{+2}$, $Zn^{+2}$, $Co^{+2}$, or $Ni^{+2}$. Preferred chelation groups include, but are not limited to, carboxylates, malonates, hydroxamates, and thiolates, such as mercaptoketones, and mercaptoalcohols. In some embodiments, for example with malonate or carboxylate, the chelation group, typically in a protected format, will be present throughout the synthetic sequence. According to other embodiments, for example with hydroxamates, the chelation group will be introduced via a post-cyclization transformation as described in more detail below.

The amino acid derivatives described herein may include one or more protecting groups to prevent unwanted side reactions during various steps of the synthesis of the desired diketopiperazines. Such protecting groups and methods for attaching and removing these groups are known commonly in the art, see, e.g., Green and Wuts, Protective Groups in Organic Chemistry (Wiley 1992) and Grant, Synthetic Peptides: A User's Guide, Grant, Ed. (Freeman 1992). Preferred protecting groups include Fmoc and BOC groups for protecting the α-amino group of the second amino acid derivative from unwanted side reactions. Protecting groups may also include photolabile or photoreactive protecting groups, such as those described in co-pending U.S. Pat. No. 5,489,678, and U.S. Pat. No. 5,143,854, each of which incorporated herein by reference.

B. The Solid Support

The support upon which the diketopiperazines are synthesized may be any solid support which is compatible with peptide synthesis, such as those described in Grant and Atherton, Solid Phase Peptide Synthesis: A Practical Approach, Atherton, et al., Eds. (IRL Press 1989). Generally, these supports may comprise glass, latex, cross-linked polystyrene and other similar polymers and resins, gold and other colloidal metal particles. Other materials will be familiar to those of skill in the art. A preferred support includes polymer-supported anisaldehyde resins, such as resin-bound 2-methoxy-4-oxy-anisaldehyde or 4-oxyanisaldehyde, which can be made from commercially available resin backbones such as TentaGel S AC or TentaGel PHB (Rappe Polymere, Tübingen, Germany) by oxidation using conventional methods such as reaction of the resin backbone with pyridinium sulfur trioxide or dimethylsulfoxide/oxalyl chloride. Another preferred support is a polymer-supported bromoacetamide resin, which can be prepared from commercially available backbone resins TentaGel S $NH_2$ or RAM resin (Rappe Polymere, Tübingen, Germany) or Pharmacia Mono A resin (Pharmacia, Piscataway, N.J.) by reaction with bromoacetic acid using standard methods. Yet another preferred support includes a resin-bound Knorr-type linker, i.e., a benzhydryl or benzylamine derivative which releases an amide or acid upon cleavage. This may be attached to the resin by the reaction of the resin with p-[(R,S)-α-[1-(9H-fluoren-9-yl)-methyloxyformamido]-2,4-dimethoxybenzyl] phenoxyacetic acid, benzotriazole-1-yl-oxy-tris-(dimethylamino)-phosphonium hexafluorophosphate and diisopropylethylamine in DMF.

The surface of the support may also comprise protecting groups such as those just described above to block one or more regions from becoming derivatized during one or more steps in the synthesis of diketopiperazines, as discussed in greater detail below. For example, where the surface of the support is derivatized with amine groups, amine protecting groups such as Fmoc may be employed to prevent reactions in those areas of the support surface so protected. The support surface may also include one or more areas protected by the photolabile groups, such as those described in U.S. Pat. Nos. 5,143,854 and 5,489,678. The use of photolabile protecting groups allows the employment of photolithographic techniques to produce a support having a large density of diverse diketopiperazine compounds at known locations on the support surface.

As noted above, the support may contain linker or spacer molecules which anchor the first amino acid derivatives to the support surface. A variety of linkers are well known in the art (See, e.g., Grant, supra), and are described in Applicants' co-pending U.S. patent application Ser. No. 08/146,886, which is incorporated herein by reference. Generally the linkers are chosen to have lengths which allow the molecules to which they are attached sufficient exposure to reagents and/or receptors which may be under study. The linkers may also be chosen to impart desired hydrophobic, hydrophilic, or steric properties. For example, linkers with bulky side chains, such as tert-butyl side chains, may be used to provide rigidity or control spacing on the support. The linker will typically include a functional group to which the first amino acid derivative is attached. This functional group may be protected initially so as to permit activation of the surface-bound linkers in selected areas of the support only. Preferred linkers include anisaldehyde derivatives such as 2- or 4-alkoxy- benzylamine or benzyl alcohol, bromoacetic acid and the Knorr linker or a similar linker, i.e., a benzhydryl or benzylamine derivative which releases an amide or acid upon cleavage. Also preferred are oligonucleotide linkers comprising one or more restriction sites which may be cleaved selectively by a restriction enzyme.

C. Coupling Conditions

For each of the methods described herein, a second amino acid derivative is coupled to a bound first amino acid derivative (optionally, mono-alkylated as in the preparation of N-alkylated diketopiperazines) to yield a bound dipeptide derivative. Prior to coupling the second amino acid to the bound first amino acid, the protecting group, if present, on the amino group of the bound first amino acid is generally removed. Typically, standard deprotection conditions known in the art can be used. For example, removal of an Fmoc may be performed with 20% to 55% of a secondary amine base such as piperidine in a polar, aprotic solvent such as DMF, methylene chloride or N-methylpyrrolidine. Typically, deprotection is achieved in about 5 minutes to one hour, but this time may be varied if oligonucleotide tagged libraries are used (see below) which may be sensitive to these reaction conditions. Depending on the choice of amino acid, solvent and base, a precipitate comprising an amine salt may occur after standing for a short period. In a preferred embodiment, the Fmoc protecting group of the first amino acid is removed by reaction of the bound derivative with a 30% piperidine/dimethylformamide solution.

A tertiary amine base, such as DBU, may also be used to remove the Fmoc group. Typically a solution of about 2% to 10%, preferably 5% DBU, in a polar, aprotic solvent such as DMF is used. However, if oligonucleotide tags are used, care should be taken as DBU has been noted to cause base modification, Palom, et al., *Tetrahedron Lett.*, 34:22195–2198. Also, following removal of Fmoc with DBU, the resin should be washed immediately to remove reactive Fmoc intermediates. Typically, these reactions are performed at room temperature, although the reaction mixture may be heated or cooled to enhance or retard the rate of reaction.

The bound first amino acid or derivative having a free (i.e., unprotected) terminal amino group is next reacted with a second amino acid derivative under conditions effective for the formation of the corresponding dipeptide. Generally, in multicomponent reaction schemes, the second amino acid derivative includes a protecting group for the α-amino moiety of the free amino acid. A preferred protecting group is Fmoc or BOC. A photolabile protecting group such as described above may also be employed. Many other protecting groups for the α-amino group are known in the art (see, e.g., Green and Wuts, Grant or Atherton, supra).

III. Synthesis of Diketopiperazines

A. Multicomponent Reaction Synthesis of Diketopiperazine Derivatives

In an alternate aspect, diketopiperazine derivatives and libraries may be synthesized using multicomponent reactions. Use of multicomponent reactions has been previously described in solid phase synthesis of other compounds. See, e.g., Armstrong et al., Acc. Chem. Res. 29:123–131 (1996). In particular, these multicomponent reactions employ a 'one-pot' reaction which combines an amine, typically in the form of a solid support bound amino acid (the solid supporst is designated by "X"), a carboxylic acid in the form of, e.g., a free amino acid, typically an N-protected natural or unnatural amino acid or amino acid derivative, an isocyanide and an aldehyde or ketone. The resulting reaction yields a support bound dipeptide or dipeptide derivative, which, upon deprotection and cyclization yields a free diketopiperazine derivative.

B. Synthesis

A schematic illustration of the multicomponent synthesis of diketopiperazines, employing an aldehyde, is shown below:

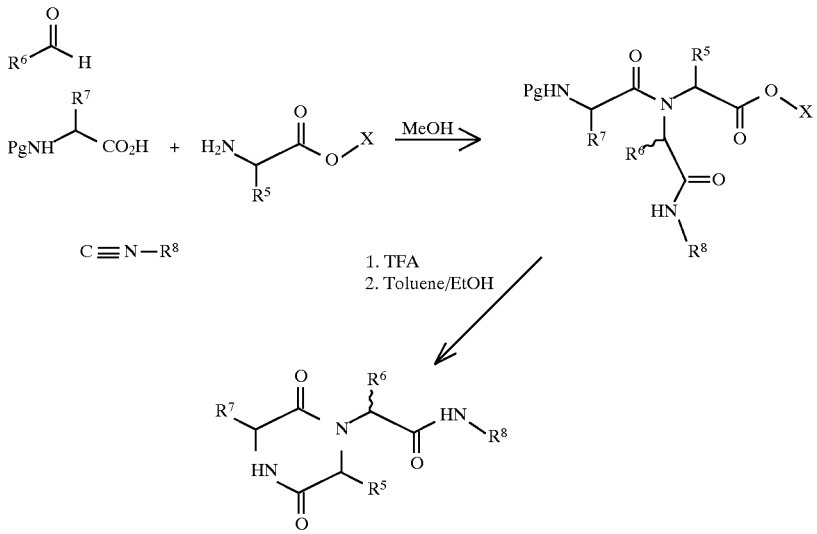

where Pg denotes a protecting group and X denotes a solid support.

The above-illustrated synthesis method is extremely flexible with regard to the specific side chain structures for the component reactants utilized in the multicomponent reaction, and these component reactants may generally be selected to provide for any number of desired derivative structures. Generally, for example, $R^5$, $R^6$, $R^7$ and $R^8$ may generally be any side chain groups. In preferred aspects, $R^5$, $R^6$, $R^7$ and $R^8$ are independently selected from hydrogen, alkyl, aryl, heteroaryl, aralkyl, heteroaralkyl, acyl, alkoxyl, aryloxyl, mercapto, alkylthio, arylthio, hydroxyl, cyano, halogen, amino (typically protected), and amido. Particularly preferred substituents for the amino acid constituents, e.g., $R^5$ and $R^7$, include those found on naturally occurring amino acids, such as benzyl, hydroxymethyl, thiomethyl, methyl, hydrogen, iso-propyl, iso-butyl, imidazolylmethyl, indolylmethyl, 4-aminobutyl, ethoxyl, 2-methylthioethyl, 3-guanidylpropyl, 2-carboxyethyl, 2-amidoethyl, or the like. Other amino acid derivatives include α,α-disubstituted amino acids. In the case of amino or carboxylated side chains, it will generally be desirable to provide these amino acids in protected form, e.g., having a suitable protecting group coupled thereto, in order to prevent the occurrence of unwanted side reactions at these groups.

Generally, the above reactants are combined in a single reaction mixture, under conditions which are conducive to formation of the dipeptide derivative. Typically, the multicomponent reaction may generally be carried out in alcohol solutions, e.g., ethanol, methanol or ethanol/dichloromethane mixtures with acceptably high yields. In some cases, it may be desirable to introduce the carbonyl component to the reaction first, in order to induce imine formation. Generally formation of the imine is performed in a solvent which is capable of solvating the reactive species involved, such as a polar solvent, under conditions effective to remove water, as this is generated by the formation of the imine. For example, solvents having a higher boiling point than water may be used in conjunction with a trap so that on reflux of the solvent, the water is removed from the system by collection in the trap. Alternatively, drying agents, such as molecular sieves, may be used to trap water in situ upon its formation. Preferred dehydrating agents include molecular sieves, magnesium sulfate, sodium sulfate, trimethyl orthoformate, zinc chloride, and the like. More preferably, the dehydrating agent is in a form which can be easily washed away from the solid support or is even used as the solvent. Most preferably, the dehydrating agent comprises trimethylorthoformate. Typically, the soluble components, e.g., aldehyde or ketone, isocyanate, free amino acid derivative, are provided at from 5 to about 25 fold molar excess over the concentration of the support bound amino acid derivative. The soluble components are generally provided at approximately equimolar ratios, although those of ordinary skill will appreciate that some variation will be tolerated. In preferred aspects, the soluble components are provided at from about 0.3 to about 0.5 M.

For the aldehyde or ketone component, reaction times can widely vary depending upon whether an aliphatic aldehyde, an aromatic aldehyde or ketone is used. In the case of aromatic aldehydes and ketones, reaction times are substantially longer and must be adjusted accordingly. As such, where $R^6$ is an aromatic group or where a ketone is substituted for the aldehyde component, e.g., where the H is substituted with an alkyl, aryl or other organic group, the reaction time must be appropriately increased. Again, these compounds are typically commercially available, or may be prepared by well known synthesis procedures.

The reaction of the constituent reactants results in a dipeptide derivative bound to a solid support having the general structure:

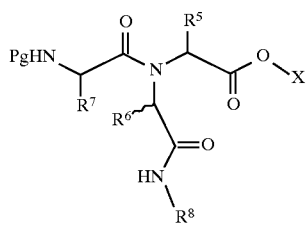

This compound may then be cyclized to form a diketopiperazine derivative. As can be seen from the structure, cyclization of the dipeptide into the diketopiperazine derivative results in cleavage of the compound from the support. This provides an advantage over other synthesis methods in that it includes an inherent purification mechanism. Specifically, reaction by-products that are not cyclized under the cyclization conditions will not be released from the support, providing a simple method for their removal from the properly cyclized compounds, e.g., filtration of the solid support, centrifugation, or the like. Also advantageous in this multicomponent approach is that it permits incorporation of sterically hindered amino acids, such as valine, into the synthesis scheme.

As noted above, the free amino acid is typically an N-protected amino acid to prevent premature reaction at the protected amine. Subsequent deprotection of the amine group permits cyclization of the support bound dipeptide, thereby releasing the compound from the support. A variety of protecting groups may generally be used for protection of the amine group, including acid or base labile protecting groups described in, e.g., Merrifield, *J. Amer. Chem. Soc.* 85:2149–2456 (1963), Atherton, et al., *Solid Phase Peptide Synthesis. A Practical Approach*, IRL Press, Oxford (1989), and Merrifield, *Science* 232:341–347 (1986). Similarly, other protecting groups may also be employed in the synthesis scheme, e.g., photolabile protecting groups, like those described in U.S. Pat. Nos. 5,143,854 and 5,489,678, previously incorporated by reference. By way of example, in the case of Fmoc/BOC protected amino acids, standard procedures may generally be used, e.g., suspension in 20% piperidine/DMF for Fmoc deprotection, and suspension in 50% TFA/DCM for BOC deprotection. Cyclization of the deprotected dipeptide derivative may then be carried out by suspending a support bound N-alkylated dipeptide in toluene or toluene/ethanol in the presence of acetic acid (e.g., 1%) or triethylamine (e.g., 4%). Typically, basic cyclization conditions are preferred over acidic conditions, for their faster cyclization times. As a result of these faster cyclization times under basic conditions, it is generally preferred to use acidic deprotection conditions, e.g., using acid labile protecting groups, and thereby prevent premature cyclization.

Isocyanides for use in the multicomponent reaction scheme are generally widely available from commercial sources. Additionally, a wide variety of additional isocyanides may be prepared using known synthesis schemes from amino acid or amine precursors. See, e.g., Ugi, Organic Chemistry, pp. 145–199 (Blomquist Ed. Academic Press, New York and London 1971), Geisemann, et al., J. Chem. Res. (S) 79 (1982), Burger, et al., J. Fluorine Chem. 65:149–152 (1993). Winitz, et al, J. Amer. Chem. Soc. 78:2423 (1956).

Figure 2:
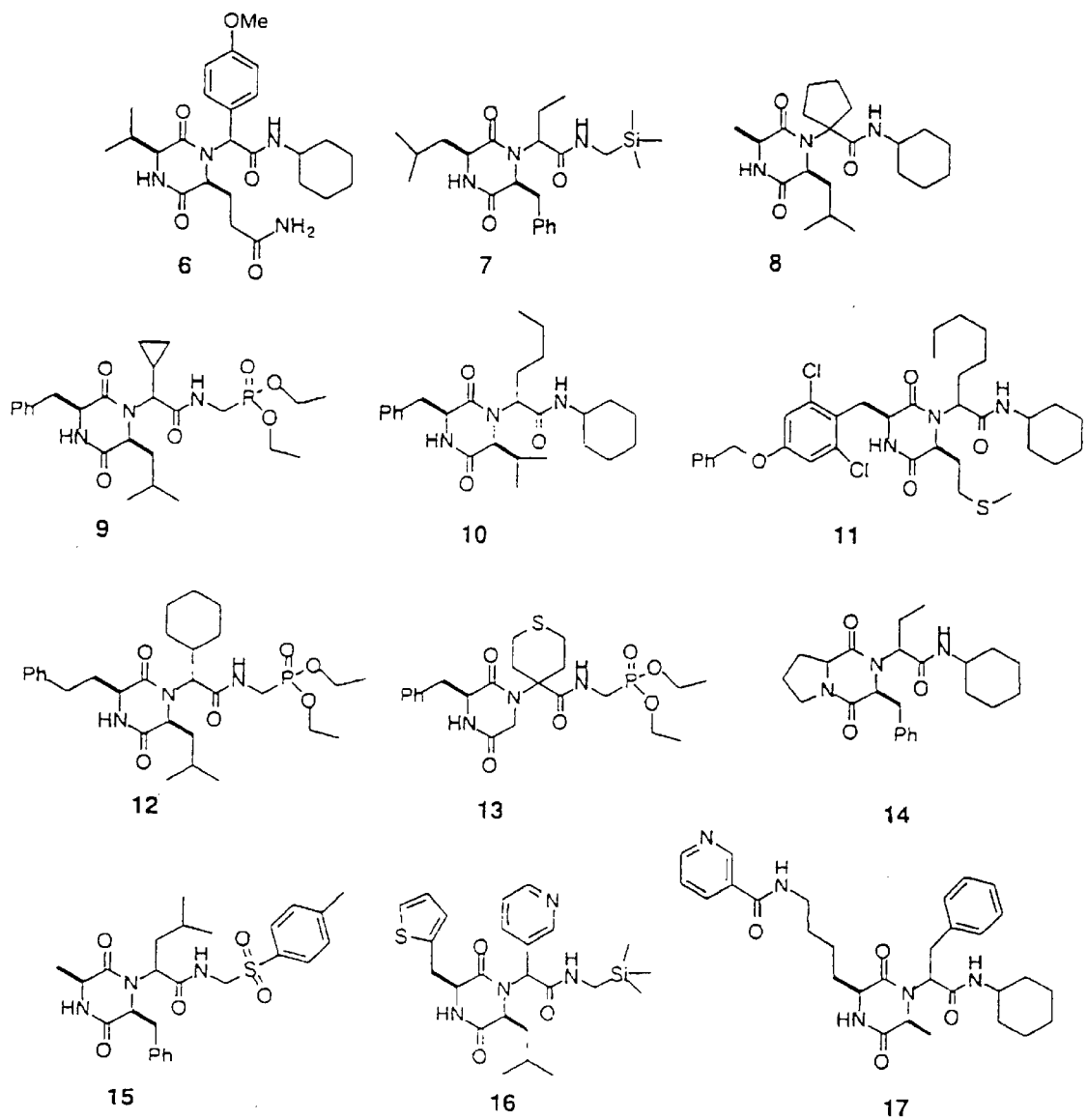
FIG. 2 shows examples of diketopiperazine derivatives synthesized utilizing a multicomponent reaction scheme.

Although generally described in terms of synthesis of single compounds, it will be appreciated that the multicomponent reaction schemes can also be used in synthesis of libraries of diverse diketopiperazine derivatives, as described in greater detail below. Examples of the structurally diverse diketopiperazines synthesized utilizing this multicomponent reaction scheme are shown in FIG. 2.

IV. Multicomponent Synthesis of Diketomorpholines

A Similar reaction scheme may be employed for the synthesis of diketomorpholine derivatives or libraries thereof. Generally, these compounds may be used in a number of applications. For example, as described above, diketomorpholine compounds have been found to possess some pharmacalogical activity, e.g., as acyl-coA inhibitors. See, Hasumi et al. J. Antibiot. 46:1782–1787 (1993). Alternatively, these diketomorpholine compounds also may be used as control compounds in ascertaining the effects of the heterocyclic amine of the corresponding diketopiperazine derivative.

Synthesis of diketomorpholine derivatives may generally be carried out in substantially the same manner as used for diketopiperazine derivatives, as described above, e.g., a multi-component reaction. Specifically, the synthesis employs an α-hydroxy acid in place of the free amino acid and results in the synthesis of an α-hydroxy acid derivative coupled to the solid support. Cyclization of the support-bound compound then yields the free diketomorpholine derivative. A schematic illustration of this synthesis is shown below.

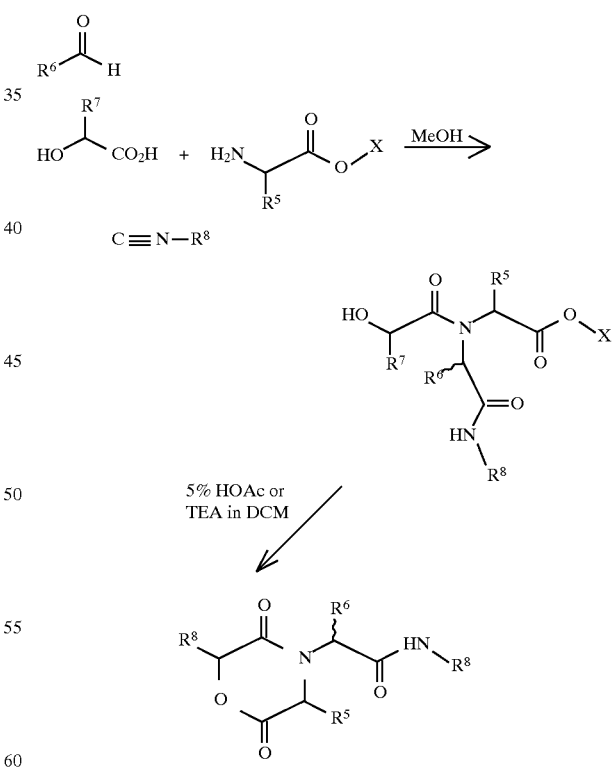

wherein $R^5$, $R^6$, $R^7$, $R^8$, Pg and X are as described above. The various reactants are generally supplied in concentrations and ratios as described for diketopiperazine synthesis.

Figure 3:
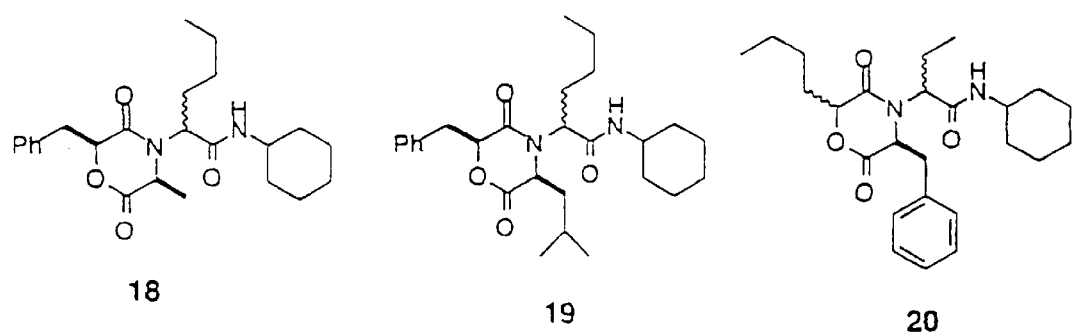
FIG. 3 shows examples of diketomorpholine derivatives synthesized utilizing a multicomponent reaction scheme.

Examples of diketomorpholine derivatives synthesized using this multicomponent reaction scheme are shown in FIG. 3.

V. Preparation of Homo-Diketopiperazines

One of skill in the art will readily appreciate that if either the first or second amino acid derivatives (e.g., the support bound or free amino acids) comprises a beta-amino acid derivative rather than an alpha-amino acid derivative, then homo-diketopiperazines having a 7-membered ring can be produced. Many beta-amino acids are commercially available, for example from Aldrich Chemical Co., Milwaukee, Wis. and Bachem Biosciences, Philadelphia, Pa.

Beta-substituted beta amino acids can be readily prepared via the Arndt-Eistert reaction with the corresponding alpha-substituted alpha amino acid (i.e., treatment with oxalyl chloride, followed by diazomethane). Conditions for effecting this transformation are described in Patai "The Chemistry of Diazonium and Diazo Compounds", Wiley, N.Y. (1978) pp. 593–644; Chaturredi et al. (1970) *J. Med. Chem.* 13:177 and Marini et al. (1992) *Synthesis* 1104 (1992).

Multicomponent synthesis schemes may generally be used in the synthesis of homo-diketopiperazines (benzo[e][1,4]diazepine-2,5-dione) derivatives. Armstrong et al., J. Am. Chem. Soc. 118:2574 (1996) reported the use of a multicomponent synthesis reaction to build up a precursor on a solid support which was then cyclized to yield an N-unsubstituted benzo[e][1,4]diazepine.

In the methods of the present invention, a support bound amino acid is employed as the amine component which is then combined with an aldehyde, isocyanide and anthranilic acid derivative under suitable reaction conditions, e.g., in methanol solutions. A general synthetic route is shown below:

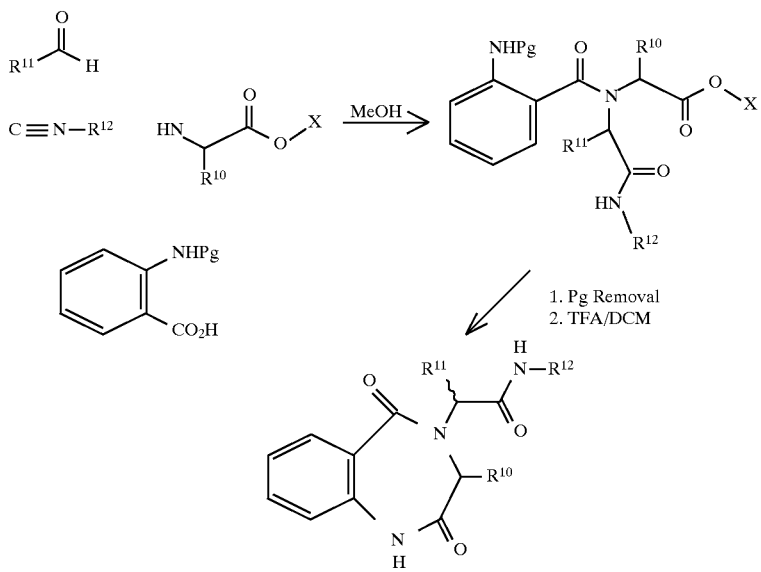

Chiral alpha-substituted beta amino acids can be prepared as shown in FIG. 1. The carboxylic acid intermediate 27 can be prepared using Evans methodology. See Evans et al. *J. Amer. Chem. Soc.* 104:1737 (1982). Curtius rearrangement, followed by hydrolysis and deprotection provides the desired alpha-substituted beta amino acid. See Banthorpe, in Patai, "The Chemistry of the Azido Group", pp. 397–405, Interscience, New York (1971); Pfister and Wyman (1983) *Synthesis* 38. This synthesis is described in detail in copending application Ser. Nos. 08/393,318 and 08/149,675, previously incorporated herein by reference.

In a preferred aspects, the synthesis employs a beta amino acid, preferably in the form of anthranilic acid, isatoic anhydride, or a substituted anthranilic acid to afford benzodiazepine-1,4-diones of the general formula:

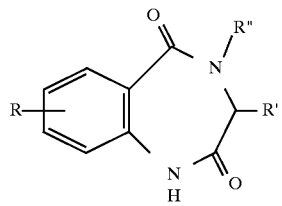

where X and Pg are a solid support and a protecting group respectively, as described above, and $R^{10}$, $R^{11}$, and $R^{12}$ may generally be any side chain group, as described above for $R^5$, $R^6$ and $R^8$, respectively, e.g., independently selected from hydrogen, alkyl, aryl, heteroaryl, aralkyl, heteroaralkyl, acyl, alkoxyl, aryloxyl, mercapto, alkylthio, arylthio, hydroxyl, cyano, halogen, amino, and amido. Useful solid supports include hydroxy resins, such as Wang, TentaGel or PAM resins, with TentaGel resins being generally preferred.

Figure 4:
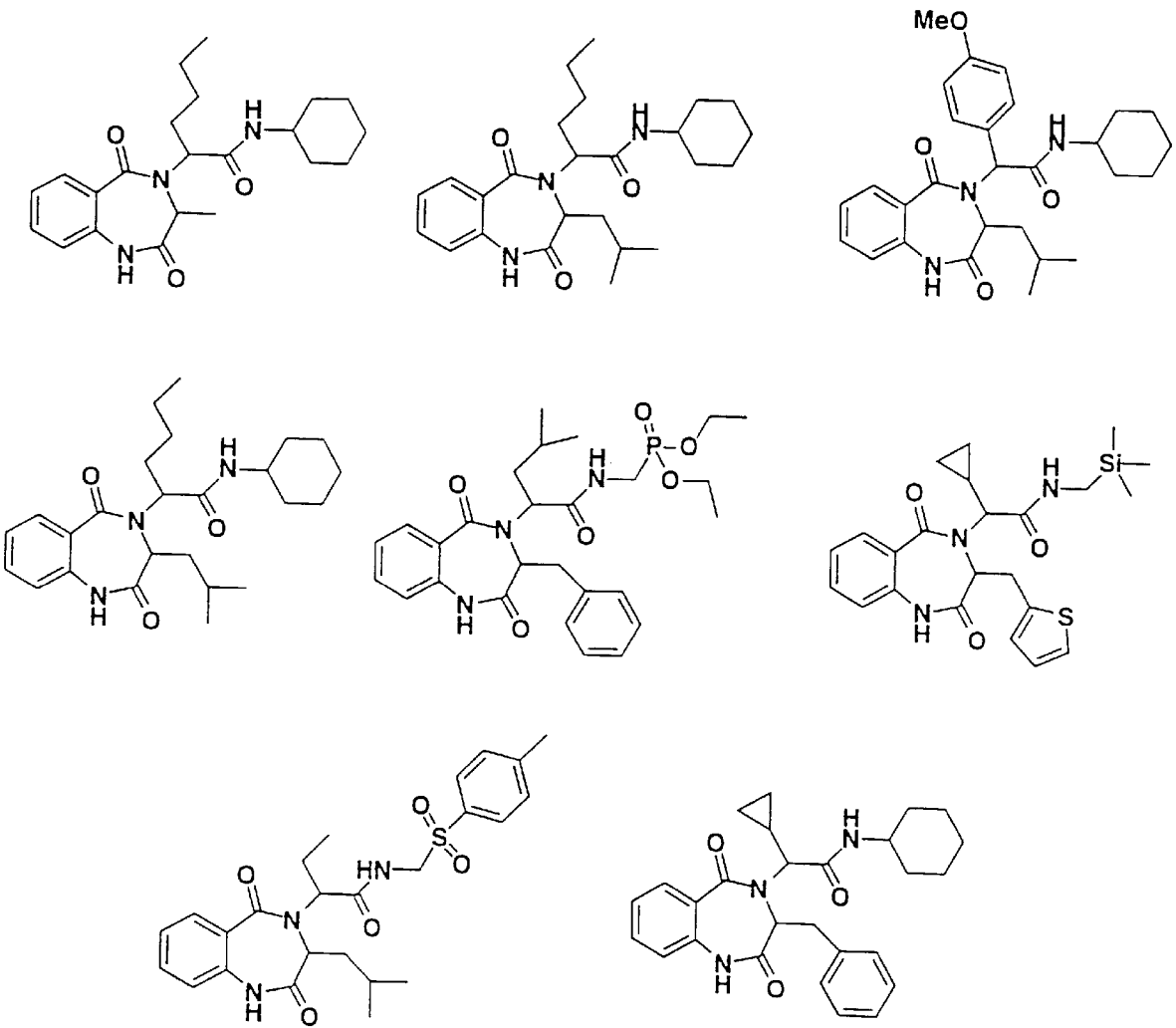
FIG. 4 shows examples of homodiketopiperazines derivatives that may be prepared utilizing the multicomponent synthesis schemes of the present invention and illustrates the structural diversity tolerated by the method.

As in the multicomponent synthesis of diketopiperazines and diketomorpholines, aliphatic or aromatic aldehydes may generally be employed. However, in the case of aromatic aldehydes, final cleaved mixtures were found to be contaminated with varying levels of aldehydes. Without being bound to a particular theory, it is believed that this is the result of imine formation between the excess aldehyde and the anilic amine group, which was subsequently cleaved under the acidic cyclization conditions. Accordingly, in particularly preferred aspects, the anilic amine of the anthranilic acid is also protected with a suitable protecting group, e.g., Fmoc, and particularly where aromatic aldehydes are used. Some examples of the structurally diverse homo-diketopiperazines synthesized according to these methods are shown in FIG. 4.

Figure 5:
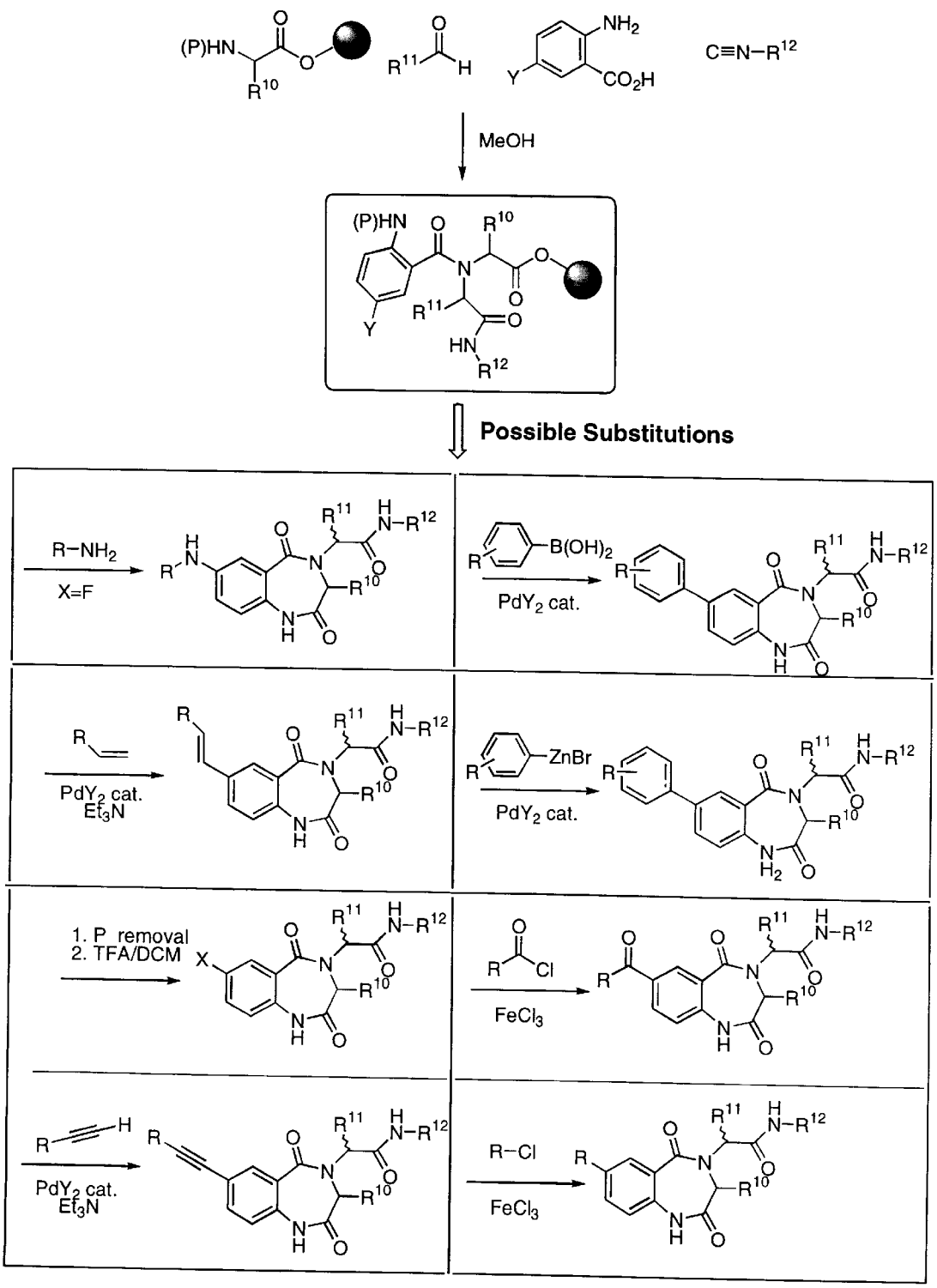
FIG. 5 shows examples of additional homodiketopiperazine compounds synthesized using a multicomponent synthesis reaction to produce the basic scaffold followed by additional synthetic steps to further derivatize the scaffold.

Further homo-diketopiperazines, derivatives or homologs thereof, may be prepared through modification of the scaffold, post synthesis. A general reaction scheme for this synthesis is shown below:

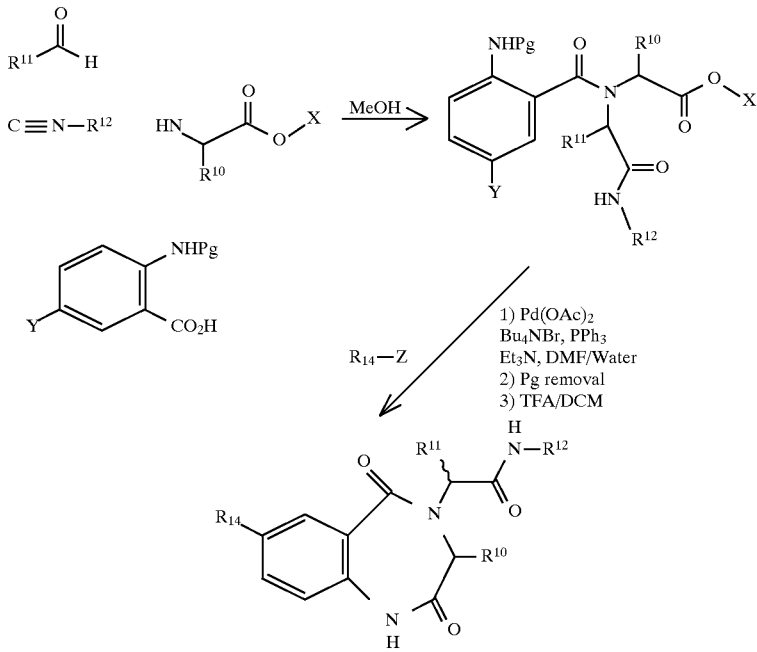

where X, Pg, $R^{10}$, $R^{11}$, and $R^{12}$ are as described, above, Y is selected from halogen, hydrogen, OTf, and Sn(alkyl)$_3$, $R^{14}$ is generally selected from hydrogen, alkyl, alkenyl, alkinyl, aryl, heteroaryl, aralkyl, heteroaralkyl, acyl, alkoxyl, aryloxyl, mercapto, alkylthio, arylthio, hydroxyl, cyano, halogen, amino, and amido, and Z is selected from halogen, amino, hydrogen, —B(OH)$_2$, OTf (also termed triflate), or Sn(alkyl)$_3$. As with the syntheses described above, a wide range of different homodiketopiperazine compounds, derivatives and analogs can be prepared utilizing these methods. Several examples of these compounds, including the additional synthetic step required to achieve the compound, are shown in FIG. 5.

VI. Chelating Groups

In some cases, a chelating group may be introduced as a substituent off of the diketopiperazine ring. As discussed above, the chelating group, optionally in a protected form, may be present throughout the preparation of the diketopiperazine ring skeleton. In a preferred embodiment, the chelating group will comprise a carboxylate, malonate, hydroxamate, or thiolate group, such as a mercapto alcohol or a mercapto ketone.

Other embodiments provide for post-cyclization transformation of the carboxyl group to yield alternative chelating groups. For example, the carboxyl group can be converted to the corresponding hydroxamate. In general, hydroxamates are obtained by treating an activated carboxylic acid derivative with either hydroxylamine or an O-protected hydroxylamine. Typical O-protected hydroxylamines include t-BuONH$_2$, THPONH$_2$, and t-BDMS-ONH$_2$ where t-Bu represents the corresponding t-butyl ether, THP represents the corresponding tetrahydropyran ether, and t-BDMS represents the corresponding t-butyldimethylsilyl ether. Alternatively, treatment of the corresponding ester with hydroxyl amine yields the desired hydroxamate.

More specifically, the free base of hydroxylamine is generated by treatment of an excess of hydroxylamine hydrochloride with an excess of potassium or sodium hydroxide in a polar solvent, such as methanol. The solution is filtered and added to the O-benzyl or O-alkyl ester of the carboxylic acid to yield the hydroxamic acid. In a further alternative method, an O-protected hydroxylamine is coupled to the acid using EDC and DIEA in a nonpolar solvent, such as dichloromethane. If the acid is not soluble in dichloromethane, DMF may be added. The protecting group, if present, can then be removed using standard deprotection conditions, as known in the art.

In particularly preferred methods, an allylester of a rsin bound acid is deprotected by treatment with Pd(Ph$_3$)$_4$ in anhydrous DCM, followed by addition of trimethylsilylazide/tetrabutylammoniumfluoride. The resin is then agitated and washed in DCM and DMF. Alternatively, the fluorenylmethyl ester of a resin bound acid is deprotected by treatment with piperidine/DMF (e.g., 20% piperidine), folloed by washing with DMF. The acid is transformed to a pentafluoro phenyl ester by treatment with pentafluorophenyl trifluoroacetate/pyridine/DMF, followed by washing with DMF. To the Pfp-ester on the resin is then added trimethylsilylhydroxylamine in DMF, and the resin is shaken and washed in DMF.

In some cases, the carboxylic acid group is converted to a mercapto alcohol or ketone. Procedures for effecting this transformation can be found in co-pending application U.S. Ser. No. 08/329,420, filed Oct. 27, 1994 which is incorporated herein by reference for all purposes.

VII. Post-Cyclization Transformations

A wide variety of post-cyclization transformations are also known, see, e.g., Srinivasachari, et al., and Sammes, supra. For example, the ring nitrogen may be alkylated or acylated. Acylation or alkylation is often a useful step in forming multiple ring systems which contain the diketopiperazine structure. For example, alkylation or acylation of either or both of the $R^1$ or $R^2$ substituents may yield a ring with a nitrogen of the diketopiperazine ring adjacent the carbon to which the substituent is attached. Acylation of the amide nitrogen, followed by nucleophilic attack by the acyl group on the adjacent carbonyl may be employed to synthesize cyclols, azacyclols or thiacyclols. The C-2 and C-5 carbons may also be transformed into dithiones. Alternatively, the ring system may be oxidized to form the corresponding heteroaromatic ring, or the carbonyls may be selectively reduced. The amide units of the diketopiperazines may also be converted into mono- or bis-lactim ethers as described above. Other transformations will be apparent to those of skill in the art.

An example of the extension of the methods of the invention to synthesize other compounds containing the diketopiperazine structure involves the alkylation or acylation of one or both of the diketopiperazine amide nitrogens with a building block ([BB$^1$]) containing a nucleophile, and the subsequent insertion of the building block into the diketopiperzine structure. This is illustrated generally below. Typical building blocks include molecules that have an electrophilic moiety which is reactive toward either or both of the amide nitrogen atoms, such as an activated carboxyl group, in addition to a nucleophilic moiety, such as amine or hydroxyl group.

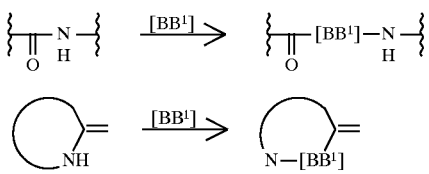

For example, acylation at an amide nitrogen with an molecule comprising a protected nucleophilic moiety (PGNu), such as protected nitrogen, oxygen or sulfur, followed by deprotection of the nucleophile and rearrangement, leads to expansion of the diketopiperzine ring by the insertion shown below. This provides a method for the synthesis of cyclols, acylamidines or expanded cyclic peptides. This synthesis is described in detail in copending U.S. application Ser. No. 08/393,318, previously incorporated herein.

By varying the reaction conditions, insertion of an amino acid or hydroxy acid, followed by nucleophilic attack on the adjacent carbonyl and, in the case of an amino acid, the elimination of water, leads to 6:5 fused ring systems. It will be appreciated that, under suitable conditions, coupling without additional cyclization or expansion may be performed. Such coupling allows for the formation of diketopiperazine chains or insertion of diketopiperazines into peptide chains. Alternatively, insertion of anthranylates can be used to produce quinazolines.

The above-described extensions can be approached in an iterative fashion. For example, in the first approach, a bound amino acid is coupled with a phenylthioamine derivative of a second amino acid to form a dipeptide which is attached to the support at the amide nitrogen (X represents any substituent). This is cyclized to form an N-phenylthiodiketopiperazine. Removal of the phenylthio substituent, followed by coupling of a third amino acid provides the amidodiketopiperazine. Deprotection of the primary amine allows the amine to attack the adjacent carbonyl carbon to form the cyclol. See, U.S. patent application Ser. No. 08/393,318.

Alternatively, the third amino acid derivative may be a N,N-phenylthio derivative. Coupling of the amino acid to the diketopiperazine, followed by reaction with triphenylphosphine to remove one of the phenylthio substituents, allows expansion to the cyclol.

VIII. Libraries of Diketopiperazines

In a preferred embodiment of the present invention, the above described solid phase synthesis is adapted to the formation of a library of diverse diketopiperazine structures, comprising a plurality of polymer beads having a plurality of surface-bound diketopiperazines. The diketopiperazines bound to each of said beads are substantially homogeneous and have a composition different from diketopiperazines bound to selected other beads. In a preferred embodiment, chemical tags are also affixed to the beads identifying the diketopiperazines synthesized thereon. These tags may include, e.g., oligonucleotide tags, or hydrocarbon or amine "hard tags". In a still more preferred embodiment, diketopiperazines and tags may optionally be cleaved, e.g. to facilitate detection or to provide a soluble library. These libraries will be referred to herein as Encoded Synthetic Libraries ("ESL"). These libraries, as well as tagging methods are described generally in co-pending U.S. patent applications Ser. Nos. 08/577,203, 08/149,675, 08/146,886, 07/946,239 and 07/762,522, and Published PCT Application No. 95/12608, the full disclosures of which are incorporated herein by reference. Such libraries can be screened to isolate individual compounds having a desired activity, e.g., receptor binding or other pharmacalogical, inhibitory or other desired property.

A general method for synthesizing such collections of diketopiperazines is described in copending U.S. application Ser. No. 08/393,318, and typically involves a random combinatorial ("stochastic") approach and the chemical and/or enzymatic assembly of amino acid monomer units. One process for producing libraries of N- or C-linked diketopiperazines comprises the steps of: (a) binding first amino acid derivatives to beads, wherein the amino acid derivatives bound on individual beads are substantially homogeneous and have a composition different from amino acid derivatives on selected other beads; (b) reacting the bound first amino acid derivatives with a plurality of second amino acid derivatives to form a plurality of dipeptide derivatives bound on individual beads that are substantially homogeneous and have a composition different from dipeptide derivatives on selected other beads; and (c) cyclizing the bound dipeptide derivatives to form a plurality of beads having diketopiperazines bound thereon, wherein the diketopiperazine derivatives bound to each bead are substantially homogeneous and have a composition different from diketopiperazines on selected other beads.

Libraries of N-alkylated diketopiperazines can also be obtained by a similar process comprising the steps of: (a) binding first amino acid derivatives to beads, wherein the amino acid derivatives bound on individual beads are substantially homogeneous and have a composition different from amino acid derivatives on selected other beads; (b) reacting the bound first amino acid derivatives with a plurality of aldehydes and a reducing agent; (c) reacting the bound N-alkylated amino acid with a plurality of second amino acid derivatives to form a plurality of dipeptide derivatives bound on individual beads that are substantially homogeneous and have a composition different from dipeptide derivatives on selected other beads; and (c) cyclizing the bound dipeptide derivatives with concomitant cleavage of the compounds from the beads to form a plurality of N-alkylated diketopiperazines.

The steps outlined in either process above may be optionally followed by steps of pooling and/or apportioning the beads among a plurality of reaction vessels or by forming a heterogeneous mixture of beads. Oligonucleotide tag components may be optically attached to the beads before, during or after each of steps (a)–(c) as described below. Typically, substantially equal numbers of solid supports will be apportioned to each reaction vessel. Those of skill in the art will recognize that the same chemical building block can be employed in different coupling steps and that the same chemical building block can be employed in more than one coupling reaction (reaction vessel) of a single coupling step.

The identifier tag has a recognizable feature that is, for example, microscopically or otherwise distinguishable in shape, size, mass, charge, or color. This recognizable feature may arise from the optical, chemical, electronic, or magnetic properties of the tag, or from some combination of such properties. In essence, the tag serves to label a molecule and to encode information decipherable at the level of one (or a few) molecules or solid supports. By using identifier tags to track the synthesis pathway that each member of a chemical library has taken, one can deduce the structure of any chemical in the library (i.e., the sequence of monomers of any oligomer) by reading the identifier tag.

The identifier tags identify each monomer coupling or other reaction step that an individual library member or solid support has experienced and record the step in the synthesis series in which each amino acid was added or other chemical reaction performed. The tags may be attached immediately before, during, or after the amino acid addition or other reaction, as convenient and compatible with the type of identifier tag, modes of attachment, and chemistry of diketopiperazines or other molecular synthesis. The identifier tag can be associated with the diketopiperazines through a variety of mechanisms, either directly, through a linking molecule, or through a solid support upon which the oligomer is synthesized. In the latter mode, one could also attach the tag to another solid support that, in turn, is bound to the solid support upon which the oligomer is synthesized. The identifier tag is added when the solid supports that have undergone a specific monomer addition or other chemical reaction step are physically together and so can be tagged as a group, i.e., prior to the next pooling step.

One can construct microscopically identifiable tags as small beads of recognizably different sizes, shapes, or colors, or labeled with bar codes. The tags can be "machine readable" luminescent or radioactive labels. The identifier tag can also be an encodable molecular structure. The information may be encoded in the size (the length of a polymer) or the composition of the molecule. Perhaps the best example of this latter type of tag is a nucleic acid sequence, i.e., RNA or DNA assembled from natural or modified bases. The tag can also comprise a variety of light-addressable molecules, such as fluorescent or phosphorescent compounds, the spectral properties of which can be changed (e.g. by photobleaching) and therefore used to store information. In one such mode, a bead incorporates a variety of fluorophors, each of which can be selectively photobleached, and so rendered incapable of fluorescence or of diminished fluorescence. During each coupling or chemical reaction step, the bead is irradiated (or not) to photobleach (or not) one or more particular types of fluorophors, thus recording the monomer identity in the oligomer synthesized.

Synthetic oligodeoxyribonucleotides are especially preferred information-bearing identifier tags. Oligonucleotides are a natural, high density information storage medium. The identity of monomer type and the step of addition or any other information relevant to a chemical synthesis procedure is easily encoded in a short oligonucleotide sequence. Oligonucleotides, in turn, are readily amenable for attachment: to a wide variety of solid supports, oligomers, linkers, and other molecules. For example, an oligonucleotide can readily be attached to a peptide synthesis bead.

Of special advantage to using oligonucleotide tags is the ability to achieve tremendous levels of target amplification through the polymerase chain reaction (PCR), see PCR Protocols: A Guide to Methods and Applications (Innis, M, Gelfand, D., Sninsky, J. and White, T., Academic Press, San Diego 1990); see also U.S. Pat. Nos. 4,683,202 and 4,965,188, and other nucleic acid replication and amplification techniques. Although the most commonly used in vitro DNA amplification method is PCR, suitable alternate amplification methods include, for example, nucleic acid sequence-based amplification, amplified antisense RNA, and the self-sustained sequence replication system. Only tiny quantities (with highly selective and efficient methods, even a single copy is sufficient) of DNA template is required for PCR, enabling one to use solid supports of microscopic dimensions and obtain larger libraries.

Libraries of free diketopiperazine derivatives or support bound intermediates, e.g., dipeptide derivatives, may also be prepared using these combinatorial synthesis methods in combination with the multicomponent synthesis schemes described above. Briefly, for example, different amino acids or amino acid derivatives may be coupled to different pools of solid supports. These supports may then be combined and reapportioned for combination with different mixtures of varied aldehyde/ketone, N-protected amino acids (or derivative), and isocyanides. By varying one or more of the individual components of the reaction, e.g., support bound amino acid, free amino acid, isocyanide, or aldehyde/ketone, one can produce large numbers of structurally diverse diketopiperazine derivatives.

In practice, library synthesis using a multicomponent reaction generally involves providing at least first and second pools of solid supports which have first and second support bound amino acids coupled thereto. The first pool of support bound amino acids are combined with a first aldehyde or first ketone, a first isocyanide, and a first free amino acid, to form a first dipeptide derivative on the support. This first dipeptide derivative may be cyclized to form a first diketopiperazine derivative. This may be done immediately following the initial synthesis or may be done at some later time, e.g., concomitently or immediately prior to screening. The second pool of support bound amino acids is combined with a second aldehyde or ketone, at least a second isocyanide, and at least a second free amino acid, to form at least a second dipeptide derivative on said support. Although described as "second" components, it will be readily appreciated that in order to produce a structurally different, e.g., "second," dipeptide derivative, one need only vary one constituent compound at a time, e.g., aldehyde, free amino acid, bound amino acid or isocyanide. Thus, at least one of the second aldehyde or ketone, the second isocyanide, the second free amino acid and the second support bound amino acid will be different from the first aldehyde or ketone, first isocyanide, first free amino acid and first support bound amino acid, respectively. As a result, at least one structural variation will be introduced into the separate pools.

The second dipeptide derivative may then be cyclized to form at least a second diketopiperazine derivative. This synthesis may then be repeated, e.g., with at least third, fourth, fifth etc., free amino acids, bound amino acids, isocyanides, and aldehydes/ketones, to produce a desired library of compounds as structurally diverse as desired.

Preferably, the libraries of diketopiperazines, diketomorpholines, their homologs and derivative, as well as mixtures thereof, are synthesized using automated procedures and instrumentation such as described in co-pending U.S. patent applications Ser. Nos. 08/149,675 and 08/146,886 and published PCT Application No. 95/12608. Alternatively, the library may formed using the Very Large Scale Immobilized Polymer Synthesis (VLSIPS™) technique, such as described in U.S. Pat. Nos. 5,143,854, 5,424,186 and 5,489,678. Briefly, the surface of the support comprises photoreactive protecting groups bound to functional groups on the support surface, e.g., amine groups. These groups are removed from selected areas of the support surface by irradiation at an appropriate wavelength through a mask or filter. A first mixture of aldehyde/ketone, isocyanide and free amino acid derivative may then be contacted with the activated substrate bound amino acid. Subsequent regions may then be activated and followed by contact with a second mixture of these soluble compounds, where at least one of the elements, e.g., the aldehyde/ketone, isocyanide or free amino acid derivative, is varied over the first mixture. Preferably a plurality of first amino acid derivatives are bound to the support surface by repeating the steps of deprotecting selected areas of the support surface and exposing the deprotected areas to a plurality of first amino acid derivatives at known locations on the support surface.

Following the various synthesis reactions, an array of diverse support bound dipeptide intermediates is created. These may then be cyclized and screeened according to the above described conditions, however, it will generally be desirable to retain each separate compound in an insular region, in order to identify the effects of a particular library member. Alternative methods include those described by Geysen, see, e,g., *J. Immune Methods*, 102:259–274 (1987), or Ellman, see, U.S. Pat. No. 5,288,514 to Ellman.

IX. Screening of Diketopiperazine Libraries

The libraries of diketopiperazines or diketomorpholines, or homologs or derivatives thereof, made according to the methods of the present invention may be screened for biological activity. Generally the library to be screened is exposed to a biological substance, usually a protein such as a receptor, enzyme, membrane binding protein or antibody, and the presence or absence of an interaction between the diketopiperazine and the biological substance is determined.

Soluble tagged diketopiperazines can be screened using an immobilized receptor. After contacting the tagged diketopiperazines with the immobilized receptor and washing away non-specifically bound molecules, bound, tagged diketopiperazines are released from the receptor by any of a wide variety of methods. The tags are optionally amplified and then examined and decoded to identify the structure of the molecules that bind specifically to the receptor. A tagged diketopiperazine in solution can be assayed using a receptor immobilized by attachment to a bead, for example, by a competition assay with a fluorescently labeled ligand. One may recover the beads bearing immobilized receptors and sort the beads using FACS to identify positives (diminished fluorescence caused by the library molecule competing with the labeled ligand). The associated identifier tag is then amplified and decoded.

In addition to identifying lead compounds, the nature of the binding between the diketopiperazines identified as having binding affinity to the biological substance may be studied by forming diketopiperazine derivatives based on the structure of the identified lead compound. These derivatives may include moieties and/or other structural alterations which produce steric and/or electronic perturbations in the structure of the lead compound. Screening this "library on a theme" against the biological substance and/or derivatives or mutants of the biological substance will yield useful information about the structural features important for biological activity. Such screening may also be performed under various conditions to determine the effects of solvent, agonists or antagonists, or temperature on binding. In addition, it will be appreciated that screening of diketopiperazine libraries will have utility in identifying diketopiperazines having novel and enhanced medicinal efficacy.

The present invention is further illustrated by the following examples. These examples are merely to illustrate aspects of the present invention and are not intended as limitations of this invention.

EXAMPLES

Materials and Methods

Common reagents and solvents were purchased from Aldrich Chemical Company (Milwaukee, Wis.) or VWR Scientific. Amino acids were purchased from Aldrich, Sigma (St. Louis, Mo.), Bachem Bioscience, Inc. (Philadelphia, Pa.), Novabiochem (La Jolla, Calif.), SynPep or Peninsula Labs (Belmont, Calif.). BOP and Knorr linkers were purchased from Novabiochem. TentaGel resins were purchased from Rappe Polymere.

Example 1
Preparation of Hydroxamate DKPs on Solid Supports

To a solution of the carboxylic acid (1 eq.), EDC (1.5 eq.) and DIEA (3–4 eq.) in a nonpolar solvent, such as dichloromethane, is added an O-protected hydroxylamine (about 1.5 eq.). If the acid is not soluble in dichloromethane, DMF may be added. The reaction is performed under an inert atmosphere and can be monitored by TLC. Reaction times vary from 1–6 hours.

Example 2
Multicomponent Synthesis of Diketopiperazines and Diketomorpholines As above, all reagents and solvents were obtained from commercial suppliers and used without further purification. TentaGel S-OH, a crosslinked polyethylene hydroxy glycol resin was purchased from Rapp Polymere. PAM resin, a divinylbenzene crosslinked polystyrene hydroxy resin was purchased from NOVABIOCHEM. $^{1}$H-NMR spectra were determined at 400 MHz and $^{13}$C-NMR spectra at 101 MHz (Varian Gemini 400 instrument). Mass spectra (flow-injection ESI) were obtained on a Finnigan TSQ 7000. High resolution mass spectra were obtained on a VG ZAB 2SE (U.C. Berkeley). All compounds were purified by reverse phase HPLC using a 0. 1% TFA water/acetonitrile buffer system.

A. General Procedures

Coupling of the First Amino Acid to Hydroxy-Resin (Mitsonobu conditions). To a solution of 5 eq. N-protected amino acid (1.2 mmol) and 5 eq. of triphenylphosphine (1.2 mmol, 302 mg) in anhydrous THF (6 mL) were added 20 eq. diisopropyl azodicarboxylate (0.9 mL, 4.6 mmol) under argon in a flame dried reaction vessel. After 5 minutes TentaGel S-OH resin (0.23 mmol, 1 g) was added to the solution and shaken for 5–10 hours. The supernatant was drained and the resin washed with DMF, ethanol and ether and dried.

Coupling of the First Amino Acid to Hydroxy-Resin (Mukaiyama conditions). To a solution of 5 eq. N-protected amino acid (1.2 mmol) and 15 eq. diisopropylethylamine (3 mL, 17 mmol) in anhydrous DCM (6 mL) were added slowly 5 eq. 1,3-dimethyl-2-fluoropyridinium 4-toluenesulfonate (1.2 mmol, 357 mg) under argon in a flame dried reaction vessel. After 15 minutes TentaGel S-OH resin (0.23 mmol, 1 g) was added to the clear yellow or red solution and shaken for 5–10 hours. The supernatant was drained and the resin washed with DMF, ethanol and ether.

Removal of Fmoc/Boc Protecting groups. Standard cleavage procedures were used to remove Fmoc and Boc protecting groups. For Fmoc deprotection the resin was suspended in 20% piperidine/DMF for 15 minutes, filtered and washed with DMF, ethanol and ether. For Boc deprotection the resin was suspended in 50% TFA/DCM for 30 minutes, filtered and washed with DCM, 10% diisopropylethylamine/DMF, DMF, ethanol and ether.

Reductive Alkylation Procedure. To $H_2N$-amino acid-resin (1 eq, 200 mg, 46 μmol) suspended in trimethylorthoformate (2 mL) was added the aldehyde component (8 eq, 0.37 mmol) and shaken for 30 minutes. Acetic acid (8 eq) in methanol (0.5 mL) followed by $NaCNBH_3$ (24 eq, 1.1 mL of 1.0M solution in THF) was added and agitated for another 30 minutes. The resin was drained, washed with methanol, DMF and ether and dried. In case of unhindered small alkyl aldehydes (e.g. propionaldehyde), only methanol and no acetic acid was added.

Acylation of the Secondary Amine (using HATU). A solution of Boc amino acid (1 mmol), DIEA (3 mmol) and HATU (1 mmol) in 2.5 mL anhydrous DMF was added to RNH-amino acid resin (200 mg, 46 μmol) and shaken for 12 hours. The solution was drained and the resin washed with DMF. The coupling procedure was repeated for a second time.

Acylation of the Secondary Amine (using HOAt). Boc amino acid (1 mmol) and HOAt (1 mmol) were dissolved in 2.0 mL anhydrous DCM and 0.5 mL anhydrous DMF. DIC (1.0 mmol) was added dropwise under Argon and ice cooling and stirred for 10 minutes. Stirring was continued for another 10 minutes at room temperature, the solution was then added to RNH-amino acid resin (200 mg, 46 μmol) and mixed for 12 hours. The solution was drained and the resin washed with DMF and DCM. The coupling procedure was repeated for a second time.

Diketopiperazine formation. The deprotected N-alkylated dipeptide on resin (200 mg) was shaken in toluene or toluene/ethanol 1:1 (2 mL) in the presence of 1% acetic acid or 4% triethylamine at room temperature for several hours. Under acidic conditions the cyclization time was usually 8–12 hours, whereas basic conditions required only 2–5 hours. The resin was washed several times with ethanol, and the supernatant concentrated.

Ugi Reaction for the Formation of diketopiperazines. To $H_2N$-amino acid-resin (200 mg) suspended in DCM (1.5 mL) was added the aldehyde (1 mmol) and shaken for 30 minutes. Boc amino acid (1 mmol) in methanol (2 mL) was added followed by the isocyanide (1 mmol). The resin was shaken for 1–8 hours, depending on the aldehyde. It was then drained, washed with methanol, DMF and ether and dried. For the Boc deprotection and DKP-formation the general procedures were followed.

Ugi Reaction and Formation of Diketomorpholines. To $H_2N$-amino acid-resin (200 mg) suspended in DCM (1.5 mL) was added the aldehyde (1 mmol) and shaken for 30 minutes. The α-hydroxy acid (1 mmol) in methanol (2 mL) was added followed by the isocyanide (1 mmol). The resin was shaken for 1–8 hours, depending on the aldehyde. It was then drained, washed with methanol, DMF and ether and dried. For the DKM-formation the resin was suspended in DCM or toluene in the presence of 2% acetic acid or 2% triethylamine and shaken for 3 hours, after which the cyclization was usually complete. After draining the resin it was washed several times with DCM and the supernatant was concentrated.

B. Specific Syntheses

2-[5-Benzyl-3,6-dioxo-1-propyl-(2S, 5S)-perhydro-2-pyrazinyl]acetic acid (1)

Hydroxymethyl PAM resin was coupled with FmocAsp(OtBu)-OH (Mukaiyama conditions) and reductively alkylated with propionaldehyde. BocPhe was coupled with HOAt/DIC and after Boc-deprotection the DKP formed in 1% HOAc/toluene (12 h). Yield: 45 mg (22%). $^1$H-NMR (400 MHz, $CDCl_3$):δ=0.89 (t,J=7.3 Hz, 3 H), 1.45–1.49 (m,1 H), 1.65–1.69 (m, 1 H), 1.92 (dd, J=6.5, 16.7 Hz, 1 H), 2.10 (dd, J=3.6, 16.7 Hz, 1 H), 2.86–2.93 (m, 1 H), 3.11 (dd, J=3.6, 13.5 Hz, 1 H), 3.24 (dd, J=6.4, 13.5 Hz, 1 H), 3.59–3.67 (m, 1 H), 4.25 (m, 1 H), 4.36 (m, 1 H), 5.41 (broad s, 1 H), 7.16–7.18 (m, 2 H), 7.30–7.34 (m, 2 H), 7.50–7.54 (m, 1 H). $^{13}$C-NMR (101 MHz, $CDCl_3$):δ=11.1, 19.9, 36.9, 40.3, 46.6, 55.8, 56.5, 127.7, 128.9, 130.2, 134.9, 164.9, 168.3, 173.5. Anal. Calcd. for $C_{16}H_{20}N_2O_4$·1.5 $H_2O$:C, 57.99; H, 7.00; N, 8.45, found: C, 57.45; H,6.35; N, 8.91

3-[5-Benzyl-1-isopentyl-3,6-dioxo-(2R, 5R)-perhydro-2-pyrazinyl]propanoic acid (2)

Hydroxymethyl PAM resin was coupled with Fmoc-D-Glu(OtBu)-OH (Mukaiyama conditions) and reductively alkylated with isovaleraldehyde. Boc-D-Phe was coupled with HOAt/DIC and after Box-deprotection the DKP formed in 4% TEA/toluene (12h). Yield: 88 mg (37%). $^1$H-NMR (400 MHz, $CD_3OD$):δ=0.67–0.70 (m, 1 H), 1.09 (2 d, J=6.5 Hz, 6 H), 1.49–1.73 (m, 3 H), 1.80–1.90 (m, 1 H), 2.01–2.10 (m, 1 H), 2.15–2.32 (m, 1 H), 3.13 (dd, J=4.5, 13.7 Hz, 1 H), 3.19 (ddd, J=5.1, 10.1, 15.1 Hz, 1 H), 3.39 (dd, J=5.2, 13.7 Hz, 1 H), 3.81 (ddd, J=5.5, 9.6, 15.1 Hz, 1 H), 3.92 (dd, J=3.6, 9.6 Hz, 1 H), 4.41 (dd, J=5.2, 5.5 Hz, 1 H), 7.30–7.48 (m, 5 H). $^{13}$C-NMR (101 MHz, $CD_3OD$): δ=22.8, 27.4, 29.0, 31.1, 36.8, 40.8, 44.8, 57.9, 59.7, 128.5, 129.7, 131.4, 167.3, 169.1, 177.0. Anal. Calcd. for $C_{16}H_{26}N_2O_4$·2 $H_2O$: C, 59.67; H, 7.91; N, 8.09, found: C, 59.09; H, 7.06; N, 7.31.

3-Benzyl-6-benzyloxymethyl-1-(4-methoxybenzyl)-(3S, 6S)-perhydro-2,5-pyrazinedione (3)

TentaGel resin was coupled with FmocPhe (Mitsunobu conditions) and reductively alkylated with anisaldehyde. BocSer(OBzl) was coupled with HOAt/DIC and after Boc-deprotection the DKP formed in 4% TEA/toluene (12 h). Yield: 7.1 mg (8.3%). $^1$H-NMR (400 MHz, $CDCl_3$): δ=1.60 (dd, J=6.4, 6.4 Hz, 1 H), 3.22 (dd, J=3.4, 10.0 Hz, 1 H), 3.28 (dd, J=2.8, 10.0 Hz, 1 H), 3.44 (dd, J=2.2, 6.4 Hz, 1 H), 3.81 (s, 3 H), 3.85 (d, J=14.6 Hz, 1 H), 4.07 (dd, J=2.2, 6.4 Hz, 1 H), 4.18 (dd, J=2.8 3.4 Hz, 1 H), 4.21 (d, J=8.0 Hz, 1 H), 4.25 (d, J=8.0 Hz, 1 H), 5.54 (d, J=14.6 Hz, 1 H), 6.42 (broad s, 1 H), 6.87–6.89 (m, 2 H), 7.19–7.40 (m, 12 H). $^{13}$C-NMR (101 MHz, $CDCl_3$): δ=36.6, 46.5, 55.8, 59.0, 72.1, 73.5, 114.6, 126.9, 127.8, 128.0, 128.2, 128.7, 129.1, 130.2, 130.5, 135.2, 137.4, 159.8, 163.5, 166.7. Anal. Calcd. for $C_{27}H_{28}N_2O_4$·$2H_2O$: C, 67.48; H, 6.71; N, 5.83, found: C, 68.00; H, 6.18; N, 5.65.

6-(Cyclohexyl)methyl-1-(3-methoxypropyl)-3-(thienylmethyl)-(3S, 6S)-perhydro-2,5-pyrazinedione (4)

TentaGel resin was coupled with FmocThiAla (Mitsunobu conditions) and reductively alkylated with anisaldehyde. BocSer(OBzl) was coupled with HOAt/DIC and after Box-deprotection the DKP formed in 4% TEA/toluene (12 h). Yield: 8 mg(11%). $^1$H-NMR (400 MHz, CDCl$_3$:δ= 0.74–0.77 (m, 1 H), 1.10–1.70 (m, 14 H), 3.27 (ddd, J=5.2, 7.6, 14.4 Hz, 1 H), 3.35 (s, 3 H), 3.45 (dd, J=4.8, 10.8 Hz, 1 H), 3.58 (dd, J=3.6, 12.0 Hz, 1 H), 3.62–3.66 (m, 2 H), 3.87 (m, 1 H), 4.10 (m, 1 H), 4.52 (dd, J=3.6, 4.8 Hz, 1 H), 6.37 (broad s, 1 H), 6.81–6.84 (m, 1 H), 6.95 (dd, J=3.6, 5.2 Hz, 1 H), 7.17 (dd, J=1.2, 5.2 Hz, 1 H). $^{13}$C-NMR (101 MHz, CDCl$_3$): δ=25.9, 26.3, 26.5, 31.1, 31.4, 33.4, 33.8, 42.2, 45.0, 52.9, 59.2, 62.2, 70.9, 125.7, 127.6, 128.2, 129.7, 166.9, 167.2. HRMS: Calcd. for C$_{19}$H$_{29}$N$_2$O$_3$S (M+H): 365.1899, found: 365.1899.

2-(4-Benzyloxybenzyl)-3-isobutyl-(3S, 8aS)-perhydropyrrolo[1,2-a]pyrazine-1,4-dione (5)

TentaGel resin was coupled with FmocLeu (Mitsunobu conditions) and reductively alkylated with 4-benzyloxybenzaldehyde. BocPro was coupled with HOAt/DIC and after Boc-deprotection the DKP formed in 4% TEA/toluene(12h). Yield: 15 mg(18%). $^1$H-NMR (400 MHz, CDCl$_3$): δ=0.77 (d, J=6.6 Hz, 1 H), 0.92 (d, J=6.6 Hz, 1 H), 1.64–1.67 (m, 1 H), 1.92–2.07 (m, 5 H), 2.48–2.50 (m, 1 H), 3.45 (ddd, J=3.4, 11.2, 12.8 Hz, 1 H), 3.75–3.78 (m, 1 H), 3.89 (d, J=15.1 Hz, 1 H) 3.98 (m, 1 H), 4.17 (ddd, J=1.2, 6.4, 9.2 Hz, 1 H), 5.06 (s, 2 H), 5.43 (d, J=15.1 Hz, 1 H), 6.92–6.94 (m, 2 H), 7.13–7.16 (m, 2 H), 7.33–7.44 (m, 5 H). $^{13}$C-NMR (101 MHz, CDCl$_3$):δ=22.2, 24.0, 24.9, 29.9, 37.6, 45.8, 57.9, 59.7, 70.5, 115.6, 127.1, 128.4, 128.9, 129.5, 136.9, 158.8, 165.6, 167.5. HRMS: Calcd. for C$_{25}$H$_{31}$N$_2$O$_3$ (M+H): 407.2335, found: 407.5327.

3-[1-Cyclohexylcarbamoyl(4-methoxyphenyl)methyl]-5-isopropyl-3,6-dioxo-(2S,5S)-perhydro-2-pyrazinyl] propanamide (6)

Gln-PAM resin was treated with anisaldehyde, BocVal and cyclo-hexyl isocyanide according to the general procedure for the Ugi reaction. Yields (isomers separated by HPLC): isomer A 34 mg (63%), isomer B 2 mg (4%). For isomer A: $^1$H-NMR (400 MHz, CDCl$_3$): δ=0.99–1.14 (m, 10 H), 1.25–1.36 (m, 2 H), 1.53–1.66 (m, 3 H), 1.80–1.93 (m, 3 H), 2.25–2.36 (m, 4 H), 3.70–3.85 (m, 2 H), 3.82 (s, 3 H), 5.39 (broad s, 1 H), 5.60–5.64 (m, 1 H), 6.28 (broad s, 1 H), 6.70 (broad s, 1 H), 6.89–7.10 (m, 2 H), 7.38–7.42 (m, 2 H). $^{13}$C-NMR (101 MHz, CDCL$_3$):δ=16.3, 17.5, 22.8 23.6, 28.1, 29.5, 30.8, 30.9, 31.3, 31.4, 47.2, 53.6, 56.5, 59.5, 59.8, 113.1, 129.5, 158.5, 164.5, 166.4, 167.1, 175.0. HRMS: Calcd. for C$_{25}$H$_{37}$N$_4$O$_5$ (M+H): 473.2764, found: 473.2762.

1N-(trimethylsilylmethyl)-2-[3-benzyl-6-isobutyl-2,5-dioxo-(3R,6R)-perhydro-1-pyrazinyl]butanamide (7)

Phe-PAM resin was treated with propionaldehyde, BocLeu and trimethylsilylmethyl isocyanide according to the general procedure for the Ugi reaction. Yield: 49 mg (91%). Isomer ratio 2:3 (by NMR). $^1$H-NMR (400 MHz, CDCl$_3$):δ=0.13 (s, 18 H), 0.70 (dd, J=6.4, 8.0 Hz, 1 H), 0.77 (dd, J=6.4, 8.4 Hz, 1 H), 0.96–1.03 (m), 1.34–1.39 (m, 1 H), 1.72–1.77 (m, 1 H), 2.16–2.22 (m, 2 H), 2.64 (dd, J=4.6, 15.4 Hz, 2 H), 3.03 (dd, J=6.0, 15.2 Hz, 1 H), 3.06 (dd, J=6.0, 15.6 Hz, 1 H), 3.20 (dd, J=4.0, 14.0 Hz, 1 H), 3.28 (d, J=4.07 Hz, 2 H), 3.37 (dd, J=3.6, 14.3 Hz, 1 H), 3.66 (dd, J=5.2, 9.2 Hz, 1 H), 3.79–3.84 (m, 2 H), 4.19–4.21 (m, 1 H), 4.42–4.45 (m, 1 H), 4.74 (dd, J=6.6, 8.9 Hz, 1 H), 4.76–4.88 (m, 1 H), 7.06–7.10 (m), 7.20–7.28 (m). $^{13}$C-NMR (101 MHz, CDCl$_3$):δ=13.5, 22.8, 25.4, 25.6, 26.3, 32.4, 39.7, 45.8, 46.0, 56.2, 60.5, 61.5, 68.5, 74.4, 130.1, 131.1, 133.2, 136.9, 170.3, 170.4, 172.8. Anal. Calcd. for C$_{23}$H$_{37}$N$_3$O$_4$Si: C, 61.71; H, 8.33; N, 9.39, found: C, 62.48; H, 8.34; N, 9.38.

1-{1-[2-Isobutyl-5-methyl-3,6-dioxo-(2S,5S)-perhydro-1-pyrazinyl]cyclopentyl carboxamide}-cyclohexane (8)

Leu-PAM resin was treated with cyclopentanome, BocAla and cyclohexyl isocyanide according to the general procedure for the Ugi reaction. Yield: 21 mg (47%). $^1$H-NMR (400 MHz, CDCl$_3$):δ=0.91 (d, J=6.1 Hz, 3 H), 1.04 (d, J=5.8 Hz, 3 H), 1.12–1.30 (m, 4 H), 1.32–1.45 (m, 3 H), 1.32–1.45 (m, 3 H), 1.55 (d, J=7.16 Hz, 1 H), 1.51–2.05 (m, 13 H), 2.54–2.61 (m, 1 H), 2.70–2.80 (m, 2 H), 7.26 (broad s, 1 H), 7.45–7.47 (m, 1 H). $^{13}$C-NMR (101 MHz, CDCl$_3$):δ=21.3, 22.1, 22.3, 23.0, 24.0, 24.7, 25.3, 25.9, 32.7, 32.9, 34.7, 37.8, 44.7, 48.4, 52.5, 58.5, 73.6, 170.0, 170.6, 172.6. Anal. Calcd. for C$_{21}$H$_{35}$N$_3$O$_3$.H$_2$O: C, 63.77; H, 9.43; N, 10.62, found: C, 63.74; H, 8.89; N, 10.42.

3-Benzyl-6-isobutyl-2,5-dioxo-(3S, 6S)-perhydro-1-pyrazinyl(cyclopropyl) methylcarboxamidomethyl-diethylphosphonate (9)

Leu-PAM resin was treated with cyclopropanal, BocPhe and diethyl-(isocyanomethyl)-phosphonate according to the general procedure for the Ugi reaction. Yield: 47 mg (77%). Isomer ratio 2:3 (by HPLC). $^1$H-NMR (400 MHz, CDCl$_3$): δ=0.25–0.27 (m, 1 H), 0.45–0.50 (m, 1 H), 0.67–0.76 (m), 0.84–1.07 (m), 1.20–1.29 (m), 1.32–1.38 (m), 1.40–1.50 (m, 1 H), 1.58–1.72 (m), 1.82–1.89 (m, 1 H), 2.99–3.06 (m), 3.23 (d, J=10.0 Hz, 1 H), 3.27 (ddd, J=4.0, 4.0, 13.4 Hz, 1 H), 3.68–3.87 (m), 4.13–4.40 (m), 6.34–6.37 (m), 7.18–7.19 (m), 7.26–7.35 (m). $^{13}$C-NMR (101 MHz, CDCl$_3$):δ=4.1, 5.1, 5.7, 6.8, 9.0, 11.0, 16.7, 16.8, 21.6, 21.7, 23.8, 23.9, 25.025.1,34.4, 35.9, 41.4, 41.6, 43.4, 44.3, 56.4, 57.7, 57.9, 60.2, 63.3, 63.4, 63.5, 64.4, 67.9, 127.9, 128.0, 129.3, 130.0, 135.8, 135.9, 166.5, 167.6, 168.6, 168.9, 169.8, 170.4. Anal. Calcd. for C$_{25}$H$_{38}$N$_3$O$_6$P.H$_2$O: C, 57.13; H, 7.67; N, 7.49, found: C, 57.25; H, 7.92; N, 7.28.

1N-cyclohexyl-2-[3-benzyl-6-isopropyl-2,5-dioxo-(3S, 6S)-perhydro-1-pyrazinyl]hexanamide (10)

Val-PAM resin was treated with valeraldehyde, BocPhe and cyclohexyl isocyanide according to the general procedure for the Ugi reaction. Yield: 49 mg (98%), two isomers 2:3 (by HPLC): $^1$H-NMR (400 MHz, CDCl$_3$):δ=0.86–1.00 (m), 1.16–1.45 (m), 1.55–1.75 (m), 1.77–1.93 (m), 1.99–2.11 (m), 2.36–2.40 (m), 2.80–2.88 (m), 3.40–3.61 (m), 3.99 (d, J=3 Hz, 1 H), 4.20–4.27 (m), 4.82 (dd, J=7.7, 7.7 Hz, 1 H), 5.83 (broad s, 1 H), 5.89 (broad s, 1 H), 7.20–7.40 (m). $^{13}$C-NMR (101 MHz, CDCl$_3$):δ=14.2, 17.1, 17.1, 20.3, 20.4, 22.6, 22.8, 24.8, 24.9, 25.8, 26.2, 28.8, 29.0, 29.5, 30.7, 31.9, 32.8, 33.1, 41.6, 41.8, 48.4, 48.5, 57.3, 57.5, 57.9, 62.5, 70.5, 70.9, 128.0, 129.6, 129.7, 135.8, 165.9, 167.6, 167.9, 170.0, 170.9. Anal. Calcd. for C$_{26}$H$_{39}$N$_3$O$_3$.½H$_2$O: C, 69.30; H, 8.95; N, 9.32, found: C, 69.36; H, 8.91; N, 9.21.

1N-cyclohexyl-2-[3-(4-benzyloxy-2,6-dichlorobenzyl)-6-(2-methylsulfanylethyl)-2,5-dioxo-(3S, 6S)-perhydro-1-pyrazinyl]octanamide (11)

Met-PAM resin was treated with heptaldehyde, Boc-2,6-diCl-Phe(pMeOBn) and cyclohexyl isocyanide according to the general procedure for the Ugi reaction. Yield: 12 mg (22%), two isomers 2:1 (by NMR): $^1$H-NMR (400 MHz, CDCl$_3$):δ=0.85–0.91 (m), 1.18–1.4 (m), 1.42–1.53 (m), 1.58–1.65 (m), 1.66–1.78 (m), 181–1.98 (m), 2.00–2.10 (m), 2.10 (s, 3 H), 2.12 (s, 3 H), 2.15–2.31 (m), 2.42–2.55 (m), 2.94 (dd, J=9.2, 13.2 Hz, 1 H), 3.04 (dd, J=8.4, 13.2 Hz, 1 H), 3.20 (dd, J=4.2, 13.6 Hz, 1 H), 3.31 (dd, J=3.6, 13.6 Hz, 1 H), 3.60–3.64 (m, 1 H), 3.73–3.76 (m, 1 H), 3.99–4.01 (m, 1 H), 4.18–4.26 (m), 4.75 (dd, J=6.8, 7.2 Hz, 1 H), 5.26 (s), 6.15 (broad s, 1 H), 6.30 (broad s, 1 H), 6.92–6.94 (m), 6.99–7.11 (m), 7.12–7.17 (m), 723–7.34 (m), 7.37–7.38 (m). $^{13}$C-NMR (101 Mhz, CDCl$_3$):δ=14.2, 15.4, 22.7, 24.7, 24.8, 24.9, 25.7, 25.8, 26.2, 26.6, 26.7, 29.0, 29.1, 29.6, 29.9, 30.0, 31.7, 32.8, 32.9, 33.0, 33.1, 40.8, 48.2, 55.6, 57.4, 57.6, 57.7, 62.6, 65.4, 69.0, 115.6, 115.7, 127.9, 128.7, 130.7, 130.8, 131.0 132.1, 137.1, 158.6, 167.5, 168.1, 169.6. Anal. Calcd.

for C$_{35}$H$_{47}$Cl$_2$N$_3$O$_4$S.H$_2$O: C, 60.51; H, 7.11; N 6.05, found: C, 60.26; H, 6.95; N, 5.67.

Cyclohexyl[2-isobutyl-3,6-dioxo-5-phenylethyl-(2S, 5S)-perhydro-1-pyrazinyl]methylcarboxamido-methyl-diethylphosphonate (12)

Leu-TGS resin was treated with cyclohexhexylcarboxaldehyde, Boc-homo-Phe and diethyl (isocyanomethyl)-phosphonate according to the general procedure for the Ugi reaction. Yield: 54 mg (84%), two isomers 1:3 (by NMR). $^1$H-NMR (400 MHz, CDCl$_3$):δ=0.77 (d, J=6.8 Hz, 3 H), 0.79–1.00 (m), 0.86 (d, J=6.6 Hz, 3 H), 0.91 (d, J=6.4 Hz, 3 H), 0.99 (d, J=6.4 Hz, 3 H), 1.10–1.40 (m), 1.46–1.60 (m), 2.48–2.55 (m), 2.94–3.06 (m), 3.08–3.22 (m), 3.31 (dd, J=3.6, 13.6 Hz, 1 H), 3.60–3.72 (m), 3.80–4.00 (m), 4.14–4.25 (m), 4.26–4.32 (m), 6.99 (broad s, 1 H), 7.10–7.35 (m). $^{13}$C-NMR (101 MHz, CDCl$_3$): δ=16.6, 16.7, 21.3, 21.5, 23.5, 23.9, 24.9, 25.4, 25.8, 26.3, 26.5, 29.6, 30.1, 30.3, 30.5, 34.1, 34.2, 34.9, 35.7, 36.5, 41.1, 41.3, 43.3, 43.8, 56.7, 57.7, 58.2, 63.8, 63.9, 76.0, 128.2, 128.3, 129.5, 129.8, 130.0, 135.1, 135.6, 159.9, 160.3, 168.8, 169.9, 170.0. Anal. Calcd. for C$_{28}$H$_{44}$N$_3$O$_6$P: C, 61.19; H, 8.07; N, 7.64, found: C, 61.58; H, 8.67; N, 6.18.

4-[3-Benzyl-2,5-dioxo-(3S)-perhydro-1-pyrazinyl] perhydro-4-thiopyranylcarboxamidomethyl-diethylphosphonate (13)

Gly-PAM resin was treated with tetrahydrothiopyran-4-one, BocPhe and diethyl(isocyanomethyl)-phosphonate according to the general procedure for the Ugi reaction. Yield: 18 mg (31%). $^1$H-NMR (400 MHz, CDCl$_3$):δ= 1.10–1.20 (m, 1 H), 1.36 (t, J=7.1 Hz, 3 H), 1.43 (t, J=6.9 Hz, 3 H), 1.72–1.88 (m, 1 H), 2.25–2.30 (m, 2 H), 2.38–42 (m, 2 H), 2.62 (dd, J=12.6, 12.6 Hz, 1 H), 2.91 (dd, J=4.6, 13.5 Hz, 1 H), 3.00–3.06 (m, 1 H), 3.10 (ddd, J=2.4, 7.2, 15.6 Hz, 1 H), 3.31 (dd, J=3.2, 13.2 Hz, 1 H), 3.57 (d, J=1.62 Hz, 1 H), 3.85–3.94 (m, 1 H), 4.10–4.33 (m, 5 H), 4.50–4.61 (m, 1 H), 7.12–7.16 (m, 2 H), 7.25–7.30 (m, 3 H), 8.49–8.51 (m, 1 H), 9.38 (broad s, 1 H). $^{13}$C-NMR (101 MHz, CDCl$_3$):δ= 16.9, 24.9, 26.1, 32.8, 34.7, 36.3, 41.3, 46.3, 48.6, 48.8, 49.0, 49.2, 49.4, 49.6, 49.9, 57.9 64.0 64.1, 64.2, 64.3, 65.2, 128.8, 129.9, 131.9, 136.5, 168.3, 168.5, 174.5. Anal. Calcd. for C$_{22}$H$_{32}$N$_3$O$_6$PS.1.5H$_2$O: C, 50.37; H, 6.73; N, 8.01, found: C, 50.84; H, 6.43; N, 7.86.

1N-cyclohexyl-2-[3-benzyl-1,4-dioxo-(3S, 8aS)-perhydropyrrolo[1,2-a]pyrazin-2yl]butanamide (14)

Phe-PAM resin was treated with propionaldehyde, BocPro and cyclohexyl isocyanide according to the general procedure for the Ugi reaction. Yield: 25 mg (61%) two isomers 1:2 (by HPLC). $^1$H-NMR (400 MHz, CDCl$_3$):δ= 0.81–0.85 (m), 0.90 (t, J=7.3 Hz, 3 H), 0.94 (t, J=7.3 Hz, 3 H), 1.20–1.48 (m), 1.51–1.80 (m), 1.84–1.91 (m), 1.98–2.25 (m), 2.30 (dd, J=6.2, 10.4 Hz, 1 H), 3.17–3.35 (m), 3.50–3.60 (m), 3.80–3.91 (m), 4.30 (dd, J=3.6, 4.0 Hz, 1 H), 4.45 (dd, J=3.6, 4.2 Hz, 1 H), 4.64 (dd, J=6.6, 8.8 Hz, 1 H), 6.70–6.72 (m), 7.10–7.30 (m). $^{13}$C-NMR (101 MHz, CDCl$_3$):δ=10.7, 11.1, 21.2, 21.9, 22.0, 23.3, 24.9, 25.0, 25.7, 29.5, 29.6, 30.4, 33.0, 33.4, 37.8, 38.4, 44.9, 48.8, 58.1, 58.2, 58.6, 60.1, 127.7, 127.9, 128.6, 128.7, 130.4, 168.7, 170.5, 170.9. HRMS: Calcd. for C$_{24}$H$_{34}$N$_3$O$_3$(M+H): 412.2600, found: 412.2593.

1n-(4-methylphenylsulfonylmethyl)-[2-benzyl-5-methyl-3,6-dioxo-(2S, 5S)-perhydro-1-pyrazinyl]-4-methylpentanamide (15)

Phe-TGS resin was treated with isobutyraldehyde, BocAla and tosylmethyl isocyanide according to the general procedure for the Ugi reaction. Yield: 14 mg (30%), two isomers 1:2 (by NMR): $^1$H-NMR (400 MHz, CDCl$_3$):δ=0.54 (d, J=7.0 Hz, 3 H), 0.83–0.89 (m), 1.10–1.45 (m), 1.65–1.75 (m), 1.72–1.91 (m), 1.95–2.80 (m), 2.42 (s, 3 H), 2.44 (s, 3 H), 2.97 (dd, J=5.2, 14.0 Hz, 1 H), 3.07 (dd, J=4.6, 14.0 Hz, 1 H), 3.2 (dd, J=3.6, 14.0 Hz, 1 H), 3.34 (dd, J=3.6, 14.0 Hz, 1 H), 3.72 (dd, J=6.6, 8.6 Hz, 1 H), 3.90–4.00 (m), 4.13–4.14 (m, 1 H), 4.27–4.29 (m, 1 H), 4.41–4.52 (m), 4.73 (dd, J=6.0, 9.2 Hz, 1 H), 5.10 (dd, J=8.0, 14.0 Hz, 1 H), 5.17 (dd, J=8.4, 13.6 Hz, 1 H), 6.16–6.18 (m), 6.95–7.10 (m), 7.23–7.30 (m), 7.36–7.40 (in), 7.82–7.86 (m), 8.07–8.12 (m), 8.95–9.10 (m). $^{13}$C-NMR (101 MHz, CDCl$_3$):δ=20.7, 21.9, 22.4, 22.5, 22.8, 23.0, 24.8, 25.2, 36.0, 37.0, 37.9, 38.2, 38.3, 49.5, 49.7, 49.9, 50.1, 50.3, 51.5, 51.6, 55.7, 58.7, 60.1, 127.8, 128.0, 128.9, 129.0, 130.1, 130.4, 130.6, 134.8, 145.7, 159.8, 163.5, 169.2, 169.9, 170.1. Anal. Calcd. for C$_{26}$H$_{33}$N$_3$O$_5$S.2 H$_2$O: C, 58.30; H, 6.96; N 7.84, found: C, 58.75; H, 6.55; N, 7.23.

1N-trimethylsilylmethyl-2-[2-isobutyl-3,6-dioxo-5-(2-thienylmethyl)-(2S, 5S)-perhydro-1-pyrazinyl]-2-(3-pyridyl)acetamide (16)

Leu-PAM resin was treated with 3-pyridine-carboxaldehyde, BocThiAla and trimethylsilylmethyl isocyanide according to the general procedure for the Ugi reaction. Yield (two isomers separated): 8 mg (13%) isomer A, 5 mg (8%) isomer B. For isomer A: $^1$H-NMR (400 MHz, CDCl$_3$):δ=−0.02 (s, 9 H), 0.67 (d, J=6.4 Hz, 3 H), 0.68 (d, J=6.4 Hz, 3 H), 0.85–0.96 (m, 1 H), 1.00–1.12 (m, 1 H), 1.46 (ddd, J=3.6, 10.0, 13.8 Hz, 1 H), 1.59–1.67 (m, 1 H), 2.62–2.74 (m, 2 H), 3.80 (dd, J=3.6, 10.8 Hz, 1 H), 4.20–4.23 (m, 1 H), 5.34 (s, 1 H), 6.81–6.84 (m, 1 H), 6.90–6.93 (m, 1 H), 7.14–7.16 (m, 1 H) 7.41–7.43 (m, 1 H), 7.97–8.00 (m, 1 H), 8.53–8.57 (m, 2 H). $^{13}$C-NMR (101 MHz, CDCl$_3$): δ=−2.1, 21.7, 23.9, 25.2, 30.9, 35.6, 44.1, 57.8, 58.9, 61.6, 125.8, 126.1, 128.2, 133.9, 137.1, 142.5, 145.2, 146.4, 167.2, 167.6, 167.8. HRMS: Calcd. for C$_{24}$H$_{35}$N$_4$O$_3$SSi (M+H): 487.2199, found: 487.2199. For isomer B: $^1$H-NMR (400 MHz, CDCl$_3$): δ=−0.02 (s, 9 H), 0.56 (d, J=6.6 Hz, 3 H), 0.66 (d, J=6.6 Hz, 3 H), 0.75–0.85 (m, 1 H), 0.91–1.1 (m, 1 H), 1.59–1.65 (m, 1 H), 2.65–2.79 (m, 2 H), 3.29–3.38 (m, 2 H), 3.90 (dd, J=3.9, 11 Hz, 1 H), 4.23 (dd, J=5.7, 5.8 Hz, 1 H) 5.20 (s, 1 H), 6.85–6.86 (m, 1 H), 6.93–6.95 (m,1 H), 7.17–7.18 (m, 1 H), 7.27–7.40 (m, 1 H), 7.89–7.91 (m, 1 H), 8.55–8.57 (m, 2 H). $^{13}$C-NMR (101 MHz, CDCl$_3$): δ=22.0, 23.5, 25.1, 31.3, 34.9, 44.5, 57.6, 62.5, 66.9, 126.0, 126.2, 128.4, 128.6, 143.6, 143.7, 143.8, 144.1, 167.9, 168.5, 168.9.

1N-cyclohexyl-2-[2-methyl-3,6-dioxo-5-[4-(3-pyridylcarboxamido)butyl-(2S, 5S)-perhydro-1-pyrazinyl]-3-phenylpropanamide (17)

Ala-PAM resin was treated with phenylacetaldehyde, BocLys(nictoninoyl) and cyclohexyl isocyanide according to the general procedure for the Ugi reaction. Yield: 12 mg (28%), two isomers 2:1 (by NMR): $^1$H-NMR (400 MHz, CDCl$_3$): δ=1.01–1.38 (m), 1.41 (d, J=7.0 Hz, 3 H), 1.48 (d, J=7.8 Hz, 3 H), 1.50–2.10 (m), 3.05–3.18 (m, 1 H), 3.22–3.36 (m, 1 H), 3.37–4.28 (m), 5.00–5.06 (m), 6.70–6.83 (m), 7.15–7.30 (m), 7.49–7.51 (m), 7.80–7.90 (m), 8.02–8.10 (m), 8.19–8.20 (m), 8.70–8.81 (m), 9.40–9.50 (m). $^{13}$C-NMR (101 MHz, CDCl$_3$): δ=20.4, 22.9, 24.8, 25.6, 28.0, 32.7, 32.8, 33.3, 35.0, 35.3, 40.0, 40.2, 48.4, 55.6, 126.4, 127.3, 127.5, 128.9, 129.1, 133.7, 136.3, 166.6, 166.8, 168.5, 169.1, 169.2 HRMS: Calcd. for $C_{30}H_{40}N_5O_4$ (M+H): 534.3080, found: 534.3089.

1N-cyclohexyl-2-(2-benzyl-5-methyl-3,6-dioxo-(2S, 5S)-1,4-oxazin-4-yl)hexanamide (18)

Ala-TGS resin was treated with valeraldehyde, L-3-phenyllactic acid and cyclohexyl isocyanide according to the general procedure for the formation of DKM's. Yield: 24 mg (56%), two isomers 2:3 (by NMR): $^1$H-NMR (400 MHz, CDCl$_3$): δ=0.81–0.90 (m), 0.9–1.4 (m), 1.46 (d, J=7.2 Hz, 3 H), 1.55 (d, J=7.3 Hz, 3 H), 1.55–2.10 (m), 3.21–3.27 (m), 3.45 (dd, J=3.6, 15.2 Hz, 1 H), 3.49–3.56 (m), 3.65–3.75 (m), 4.24–4.34 (m, 2 H), 4.64 (dd, J=7.7, 7.9 Hz, 1 H), 5.02–5.04 (m, 2 H), 6.33–6.35 (m, 1 H), 6.48–6.50 (m, 1 H), 7.20–7.31 (m). $^{13}$C-NMR (101 MHz, CDCl$_3$): δ=14.3, 18.2, 19.1, 19.7, 22.7, 22.8, 25.1, 25.2, 25.8, 25.9, 26.0, 28.0, 28.8, 28.9, 29.4, 29.9, 32.9, 33.1, 33.2, 36.9, 37.0, 37.5, 39.9, 48.9, 49.1, 49.3, 51.6, 56.0, 56.6, 57.9, 62.4, 67.8, 127.8, 128.5, 128.9, 128.9, 129.6, 130.5, 130.8, 130.9, 135.7, 135.8, 166.7, 167.5, 167.9, 169.5, 169.9. HRMS: Calcd. for $C_{24}H_{34}N_2O_4$ (M+H): 415.2596, found: 415.2597.

1N-cyclohexyl-2-(2-benzyl-5-isobutyl-3,6-dioxo-(2S, 5S)-1,4-oxazin-4-yl)hexanamide(19)

Leu-TGS resin was treated with valeraldehyde, L-3-phenyllactic acid and cyclohexyl isocyanide according to the general procedure for the formation of DKM's. Yield: 30 mg (16%), two isomers 2:3 (by NMR): $^1$H-NMR (400 MHz, CDCl$_3$): δ=0.30–0.47 (m), 0.71 (t, J=6.4 Hz, 3 H), 0.85–0.95 (m), 1.15–1.40 (m), 1.53–1.70 (m) 1.71–1.80 (m), 1.81–2.15 (m), 3.23–3.41 (m), 3.57 (dd, J=7.6, 8.8 Hz, 1 H), 3.67–3.80 (m), 3.87 (dd, J=4.4, 11.2 Hz, 1 H), 4.10 (dd, J=3.9, 11.2 Hz, 1 H), 4.56 (dd, J=7.7, &.8 Hz, 1 H), 5.14–5.17 (m, 2 H), 6.87–6.90 (m, 1 H), 7.20–7.33 (m), 7.64–7.67 (m, 1 H). $^{13}$C-NMR (101 MHz, CDCl$_3$): δ=14.0, 20.8, 20.9, 22.5, 22.6, 22.9, 23.2, 24.7, 24.9, 25.7, 26.5, 28.3, 28.7, 29.4, 32.8, 32.9, 33.0, 39.5, 39.7, 42.4, 43.0, 48.7, 48.9, 53.8, 57.7, 60.4, 68.5, 79.4, 79.6, 128.1, 128.2, 129.1, 129.2, 130.2, 130.4, 134.5, 134.8, 165.0, 166.3, 167.1, 162.9, 170.5. HRMS: Calcd. for $C_{27}H_{41}N_2O_4$ (M+H): 457.3066, found: 457.3066.

1N-cyclohexyl-2-(2-benzyl-5-butyl-3,6-dioxo-(2S, 5S)-1,4-oxazin-4-yl}butanamide (20)

Phe-TGS resin was treated with propionaldehyde, (+/−)-2-hydroxycaproic acid and cyclohexyl isocyanide according to the general procedure for the formation of DKM's. Yield: 29 mg (35%), mixture of isomers: $^1$H-NMR (400 MHz, CDCl$_3$): δ=0.79–0.96 (m), 1.02–1.40 (m), 1.41–2.20 (m), 3.10–3.23 (m), 3.50–3.80 (m), 3.96–4.10 (m), 4.11–4.23 (m), 7.11–7.35 (m), 7.63–7.65 (m). $^{13}$C-NMR (101 MHz, CDCl$_3$): δ=12.1, 14.0, 22.3 22.4, 23.4, 23.2, 24.3, 24.6, 24.9, 25.5, 25.6, 29.4, 29.7, 29.7, 29.8, 32.3, 32.5, 32.6, 32.7, 32.8, 32.9, 34.5, 34.6, 35.3, 35.6, 35.7, 43.2, 45.6, 49.8, 60.7, 63.3, 127.2, 127.3, 127.5, 128.9, 129.1, 129.3, 129.5, 129.6, 129.8, 137.7, 138.5, 168.5, 170.6, 171.4, 171.9, 172.1, 172.2, 174.5, 174.9.

Example 3
Multicomponent Synthesis of Homo-diketopiperazines
1N-cyclohexyl-2[3-methyl-2,5-dioxo-(3S)-2,3,4,5-tetrahydro-1H-benzo[e][1,4]diazepin-4-yl]hexanamide 200 mg FmocAla-Wang resin (88 µol) were Fmoc deprotected according to standard procedures. The resin was then suspended in 1.5 ml DCM and valeraldehyde (212 µl, 2 mmol) added. The mixture was agitated for 30 minutes and cyclohexylisocyanide (256 µl, 2 mmol) and anthranilic acid (274 mg, 2 mmol) was added, in that order. The resin was mixed for 2 hours, drained, washed with DMF, EtOH and ether and dried. For the cyclization, the resin was shaken in 5% TFA/DCM for 12 hours, drained and washed with DCM. The supernatant and the collected washes were concentrated and the product purified by HPLC, yielding two isomers which could not be separated. 5.0 mg white powder (23%) resulted. NMR and mass analysis were in accordance with the structure.

While the foregoing invention has been described in some detail for purposes of clarity and understanding, it will be clear to one skilled in the art from a reading of this disclosure that various changes in form and detail can be made without departing from the true scope of the invention. All publications and patent documents cited in this application are incorporated by reference in their entirety for all purposes to the same extent as if each individual publication or patent document were so individually denoted.

What is claimed is:

1. A method of synthesizing diketomorpholine derivatives, comprising:
    providing a first amino acid derivative on a solid support;
    combining an aldehyde or ketone, an isocyanide, and an α-hydroxy acid with said first amino acid under conditions whereby an α-hydroxyacid is formed on said solid support; and
    cyclizing said support bound α-hydroxy-acid to form a diketomorpholine derivative.

2. The method of claim 1, wherein said cyclizing is carried out in toluene/ethanol/triethylamine.

3. The method of claim 1, wherein said combining is carried out in alcohol.

4. The method of claim 1, wherein said alcohol is methanol.

5. The method of claim 1, wherein said cyclizing of said support bound α-hydroxy acid to form an diketomorpholine derivative releases said diketomorpholine derivative from said solid support.

6. The method of claim 1, wherein each of said aldehyde or ketone, said isocyanide and said α-hydroxy acid is present at from about 5 to about 25 molar excess of said support bound first amino acid.

7. The method of claim 1, wherein each of said aldehyde or ketone, said isocyanide and said α-hydroxy acid is present at about equimolar ratios.

8. A method of synthesizing a diketomorpholine derivative, comprising:
    providing a first amino acid or amino acid derivative on a solid support;
    combining an aldehyde or ketone, an isocyanide, and an α-hydroxy acid with said first amino acid or amino acid derivative under conditions whereby an α-hydroxy acid is formed on said solid support; and
    cyclizing said support bound α-hydroxy-acid to form a free diketomorpholine derivative.

9. A method of producing a compound having the structure

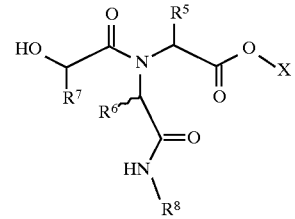

wherein X is a solid support, $R^5$, $R^6$, $R^7$ and $R^8$ are independently selected from hydrogen, alkyl, aryl, heteroaryl, aralkyl, heteroaralkyl, acyl, alkoxyl, aryloxyl, mercapto, alkylthio, arylthio, hydroxyl, cyano, halogen, amino, and amido, the method comprising:

combining compounds having the following structures:
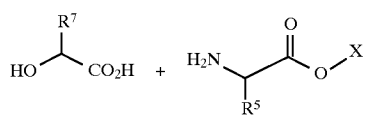
under conditions conducive to reaction of said compounds.
* * * * *